United States Patent
Kubo et al.

(10) Patent No.: US 8,273,263 B2
(45) Date of Patent: Sep. 25, 2012

(54) IONIC COMPOUND

(75) Inventors: Daisuke Kubo, Kyoto (JP); Takayuki Ueda, Kyoto (JP); Hideyuki Tahara, Osaka (JP); Keiichiro Mizuta, Akashi (JP); Hironobu Hashimoto, Kawanishi (JP); Taisuke Kasahara, Suita (JP)

(73) Assignee: Nichicon Corporation, Kyoto (JP)

( * ) Notice: Subject to any disclaimer, the term of this patent is extended or adjusted under 35 U.S.C. 154(b) by 1455 days.

(21) Appl. No.: 11/829,212

(22) Filed: Jul. 27, 2007

(65) Prior Publication Data
US 2008/0083626 A1  Apr. 10, 2008

(30) Foreign Application Priority Data

| | | |
|---|---|---|
| Jul. 27, 2006 | (JP) | 2006-204837 |
| Jul. 27, 2006 | (JP) | 2006-204838 |
| Dec. 25, 2006 | (JP) | 2006-347413 |
| Dec. 25, 2006 | (JP) | 2006-347414 |

(51) Int. Cl.
 H01G 9/035 (2006.01)
 H01G 9/022 (2006.01)
(52) U.S. Cl. ........................ 252/62.2; 361/504
(58) Field of Classification Search .............. 252/62.2; 361/504
 See application file for complete search history.

(56) References Cited

U.S. PATENT DOCUMENTS

| | | |
|---|---|---|
| 2,766,243 A | 10/1956 | Middleton |
| 2,766,246 A | 10/1956 | Middleton |
| 4,734,821 A | 3/1988 | Morimoto et al. |
| 5,587,871 A * | 12/1996 | Ue et al. .................... 361/504 |
| 6,395,367 B1 | 5/2002 | Michot et al. |
| 6,576,159 B1 | 6/2003 | Michot et al. |

(Continued)

FOREIGN PATENT DOCUMENTS

EP     0010396 A1    4/1980

(Continued)

OTHER PUBLICATIONS et al. "The Crystal Structure of Ammonium Tricyanomethide, $NH_4C(CN)_3$." Acta Cryst., 1965, vol. 18, Part 1. pp. 1-4.

(Continued)

Primary Examiner — Carol M Koslow
(74) Attorney, Agent, or Firm — Connolly Bove Lodge & Hutz LLP

(57) ABSTRACT

An ionic compound is provided that has an anion represented by a: formula (1) and a cation represented by a formula (2):

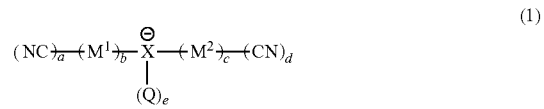

where X is an element selected from the group consisting of B, C, N, O, Al, Si, P, S, As, and Se, $M^1$ and $M^2$ are identical or different, and represent linking groups, and, when multiple $M^1$s or multiple $M^2$s are present, they may be identical or different, Q represents a monovalent element or organic group, a represents an integer of 1 or more, and b, c, d, and a each represent an integer of 0 or more; and $R_S$-$LH^{\oplus}$(2) where L is an element selected from the group consisting of C, Si, N, P, S, and O, R represents a monovalent element, functional group, or organic group, and s represents an integer of 2 to 4.

8 Claims, 8 Drawing Sheets

U.S. PATENT DOCUMENTS

2004/0002002 A1* 1/2004 Mizuta et al. ............... 429/188

FOREIGN PATENT DOCUMENTS

| JP | 54-7564 | | 1/1979 |
|---|---|---|---|
| JP | 09-097749 | | 4/1997 |
| JP | 2000-311839 | | 11/2000 |
| JP | 2004-292350 | A | 10/2004 |
| JP | 2005-353568 | | 12/2005 |
| JP | 2006-173014 | | 6/2006 |
| JP | 2006-199646 | | 8/2006 |
| JP | 2006-202646 | | 8/2006 |
| JP | 2006-216524 | | 8/2006 |
| WO | WO-2005/109562 | | 11/2005 |
| WO | WO 2005/109562 | * | 11/2005 |
| WO | WO-2006/021390 | | 3/2006 |
| WO | WO-2007/066822 | A1 | 6/2007 |

OTHER PUBLICATIONS et al., "Synthesis and Thermal Decomposition Studies of New Nitroso-and Nitrodicyanomethanide Salts," *Inorg. Chem.*, 1999, vol. 38, No. 11, pp. 2709-2715.

International Search Report.

Hantzsch et al., 'Uber Cyanoform, Chemische Berichte, vol. 32, Jan. 1, 1899, pp. 641-650, XP002673435.

Huttner et al., "Zur Raum-Chemie der Cyan-Abkömmlinge der flüchtigen Hydride", Zeitschrift Für Anorganische und Allgemeine Chemie, vol. 190, Jan. 1, 1930, pp. 27-37, XP002673436.

Elvidge et al., "Preparation of Some Highly Polarised Ethenes by the Addition of Amines to Suitable Carbonitriles", Journal of the Chemical Society, Perkin Transactions I, Chemical Society, Letchworth, GB, No. 8, Jan. 1, 1983, pp. 1741-1744, XP002061825.

Makhon'kov, "Synthesis and reactivity of Tetracyanornethane", Journal of Organic Chemistry of the USSR, M A I K Nauka—Interperiodica, RU, vol. 15, 1979, pp. 2207-2210, XP009157978.

Trofimenko et al., "Tricyanomethane (Cyanoform), Carbamyldicyanomethane, and Their Derivatives", Journal of Organic Chemistry, American Chemical Society, Easton, US, vol. 27, Feb. 1, 1962, pp. 433-438, XP001205485.

Forsyth et al., "Ionic Liquids Based on imidazolium and Pyrrolidinium Salts of the Tricyanomethanide Anion", Australian Journal of Chemistry, Csiro, AU, vol. 57, No. 2, Jan. 1, 2004, pp. 121-124, XP09157985.

Jaeger et al., "Pseudohalogenvergindungen Darstellung und reaktionsverhalten von Alkyl- und Arylammoniumdicyanamiden, -Tricyanmethaniden und Dicyanmethanidoacetaten Ärnh3ü(X = N(CN)2, C(CN)3, (C(CN)2C(O)CH3)//Pseudohalogen Compounds. Synthesis and Reactivity of Alkyl-", Zeitschrift Fur Anorganische und Allgemeine Chemie, Wiley—V C H Verlag GMBH & Co., KGAA, DE, vol. 611, Jan. 1, 1995, pp. 68-72, XP009044908.

Cioslowski et al., Unusual Bonding in the 1,1,1-triamino-2,2,2-tricyanoethane Molecule:, Chemical Physics Letter, vol. 170, No. 2,3, Apr. 16, 1990, pp. 297-300, XP002673437.

Extended European Search Report dated Apr. 18, 2012, issued in corresponding European Patent Application No. 07790995.0.

* cited by examiner (a)

(b)

( c )

IONIC COMPOUND

This application claims priority under 35 U.S.C. Section 119 to Japanese Patent Applications No. 2006-204837 filed on Jul. 27, 2006, No. 2006-204838 filed on Jul. 27, 2006, No. 2006-347413 filed on Dec. 25, 2006, and No. 2006-347414 filed on Dec. 25, 2006, which are herein incorporated by reference.

BACKGROUND OF THE INVENTION

1. Field of the Invention

The present invention relates to an ionic compound, and more specifically, to an ionic compound suitable as a material for an ionic conductor of which an electrochemical device is constituted, and an electrolyte material, an electrolytic solution, and an electrolytic capacitor each containing the ionic compound.

2. Description of the Related Art

Each of ionic compounds uses an ionic substance formed of a compound constituted of a cation and an anion as an essential ingredient, and finds use in a variety of applications. Of the ionic compounds, an ionic compound having ionic conductivity is suitably used as an ion conductive material. To be specific, the ionic compound is suitably used as a component of an ionic conductor used as an essential ingredient in, for example, any one of various cells based on ion conduction. The component of the ionic conductor can function as at least one of an electrolyte and a solvent in an electrolytic solution of which the ionic conductor is constituted. In addition, the component of the ionic conductor can function as a solid electrolyte. Examples of the applications of the component of the ionic conductor include: cells having charging and discharging mechanisms such as a primary cell, a lithium (ion) secondary cell, and a fuel cell; and electrochemical devices such as an electrolytic capacitor, an electric double layer capacitor, a solar cell, and an electrochromic display device. In each of those electrochemical devices, in general, a cell is constituted of a pair of electrodes and an ionic conductor filling a gap between the electrodes.

Currently used as the ionic conductors are electrolyte solutions prepared by dissolving an electrolyte such as lithium perchlorate, $LiPF_6$, $LiBF_4$, tetraethylammonium fluoroborate, or tetramethylammonium phthalate, in an organic solvent such as γ-butyrolactone, N,N-dimethylformamide, propylene carbonate, or tetrahydrofuran. When dissolved in the organic solvent, the electrolyte dissociates into a cation and an anion to allow ionic conduction through the electrolytic solution. Solid electrolytes which allow ionic conduction in a solid state may also be used as an ionic conductor.

FIG. 1 shows a schematic cross sectional view of an embodiment of a conventional lithium (ion) secondary battery. The a lithium (ion) secondary battery has a positive electrode and a negative electrode each formed of an active substance, and an electrolytic solution constituted of an organic solvent and a lithium salt such as $LiPF_6$ dissolved as a solute in the solvent, forms an ionic conductor between the positive and negative electrodes. During charging, the reaction $C_6Li \rightarrow 6C+Li+e^-$ occurs on the negative electrode, the electron ($e^-$) generated on the negative electrode surface migrates through the electrolytic solution to the positive electrode surface in the manner of ionic conduction. On the positive electrode surface, the reaction $CoO_2+Li+e^- \rightarrow LiCoO_2$ occurs and an electric current flows from the negative electrode to the positive electrode. During discharging, reverse reactions of those during the charging occur, and an electric current flows from the positive electrode to the negative electrode.

However, the an electrolytic solution forming an electrochemical device has the following problems: the organic solvent may readily volatilize and has a low flash point; liquid leakage may readily occur, resulting in lack in long-term reliability; and the electrolytic solution coagulates at low temperatures and therefore fails to exhibit performances as an electrolytic solution. Thus, there has been a demand for materials capable of improving those problems.

It has been disclosed that an ionic compound containing a sufficient number of anion portions (the number is not less than one) bonded to at least one cation portion M for securing entire electrical neutrality in which M represents hydroxonium, nitrosonium $NO^+$, ammonium $NH_4^+$, a metal cation having a valence of m, an organic cation having a valence of m, or an organometallic cation having a valence of m, and the anion portions each correspond to one of the formulae $R_D$—Y—C(C≡N)$_2^-$ and Z-C(C≡N)$_2^-$ can be used as an ion conductive material (see, for example, Japanese Patent Translation Publication No. 2000-508676 (p. 2 to 13 and 39 to 67)). Each of the anion portions is of a five-membered ring shape, or is a derivative of tetraazapentalene, and the derivatives of triazole, imidazole, and cyclopentadiene are described as examples of the anion portions in examples. To be specific, a tricyanomethide has been disclosed. However, there still remains a need for making contrivance in order that the compound may be a suitable material of which an electrolytic solution exerting excellent basic performance is constituted.

An electrolytic solution for driving an electrolytic capacitor prepared by dissolving a carboxylate of any one of the pentaalkylguanidines as a solute in γ-butyrolactone as an organic polar solvent has been disclosed (see, for example, Japanese Patent Application Laid-open No. Hei 9-97749 (p. 1 and 2)). However, the electric conductivity of a tertiary ammonium salt-based electrolytic solution is not sufficient as compared to that of a quaternary ammonium salt-based electrolytic solution. Accordingly, there still remains a need for making contrivance in order that an electrolytic solution capable of serving as a highly reliable electrolyte and having an additionally high electric conductivity may be developed.

An electrolytic solution for use in an electrochemical device such as a lithium secondary cell, an electrolytic capacitor, or an electric double layer capacitor is desirably excellent in an ionic conductivity and electrochemically stable at high electric potentials. To be specific, a solution prepared by dissolving a salt of, for example, triethylamine and maleic acid or phthalic acid (tertiary salt) in a solvent such as γ-butyrolactone, N,N-dimethylformamide, or ethylene glycol has been used as an electrolytic solution for an electrolytic capacitor (see, for example, Japanese Patent Application Laid-open No. Sho 54-7564). However, when a tertiary salt is used as described above, the following problem arises: the resultant solution has a low electric conductivity.

In view of the foregoing, a solution prepared by dissolving a salt of a tetraalkylammonium and, for example, maleic acid or phthalic acid (quaternary salt) in a solvent has been used (see, for example, Japanese Patent Application Laid-open No. Sho 62-264615). An electric conductivity in the case where a quaternary salt is used is higher than that in the case where a tertiary salt is used, but the case where a quaternary salt is used involves the following problem: a pH in a system increases. As a result, the following problem arises: sealing rubber for a capacitor deteriorates, and a liquid leaks from a cathode portion to adhere to the surface of a printed circuit board, thereby causing deficiencies such as corrosion and disconnection. In addition, the use of a quaternary salt increases an electric conductivity as compared to that in the case where a tertiary salt is used, but an additional increase in an electric conductivity is desired.

SUMMARY OF THE INVENTION

The present invention has been made in view of the above-mentioned circumstances, and an object of the present invention is to provide an ionic compound which: can exert excellent basic performance such as excellent electrochemical stability including an excellent ionic conductivity; is excellent in pH stability; and can suitably find use in a variety of applications, and an electrolyte material, an electrolytic solution, and an electrolytic capacitor each containing the ionic compound.

The inventors of the present invention have made various investigations on ionic compounds. As a result, the inventors have paid attention to the fact that an ionic compound having ionic conductivity out of the ionic compounds each constituted of a cation and an anion can be suitably used as an ion conductive material in a variety of applications.

For example, in the case of an ionic compound in which a cation has a hydrogen atom, the cation can react with a hydroxide ion to produce water. As a result of the foregoing, there is a low probability that the ionic compound becomes a strong alkali even in, for example, an environment where a hydroxide ion concentration becomes high. In view of the foregoing, the inventors have found that rubber or the like which is apt to deteriorate under an alkaline environment can be used, and hence can suitably find use in a variety of applications. In addition, the inventors have found that each of the ionic compound and an electrolyte material containing the ionic compound can suitably find use in a variety of applications including materials for electrochemical devices.

In a conventional electrolytic capacitor, an electrolytic solution having a high electric conductivity and using a solvent mainly formed of γ-butyrolactone and a quaternary ammonium salt as a solute has been used. When the quaternary ammonium salt-based electrolytic solution is used, a base component of the solution leaks from a cathode portion in some cases. In view of the foregoing, an investigation has been conducted on the use of a tertiary ammonium salt-based electrolytic solution causing no liquid leakage.

For example, the inventors have found that a problem possessed by a conventional tertiary ammonium salt-based electrolytic solution, that is, an insufficient electric conductivity as compared to that of a quaternary ammonium salt-based electrolytic solution can be solved by providing a cation of an ionic compound with a specific tertiary salt structure. As a result, the ionic compound can achieve compatibility between long-term reliability and a sufficient electric conductivity, and can suitably find use in a variety of applications including cells having charging and discharging mechanisms and electrochemical devices. In addition, the inventors have found that each of the ionic compound and an electrolyte material containing the ionic compound can suitably find use in a variety of applications including materials for electrochemical devices.

An ionic compound of the present invention includes:
an anion represented by a general formula (1):

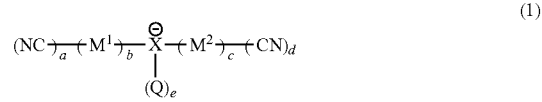
(1)

where X represents at least one kind of an element selected from the group consisting of B, C, N, O, Al, Si, P, S, As, and Se, $M^1$ and $M^2$ are identical to or different from each other, and represent linking groups, and, when multiple $M^1$s or multiple $M^2$s are present, the multiple $M^1$s or the multiple $M^2$S may be identical to or different from each other, Q represents a monovalent element or organic group, a represents an integer of 1 or more, and b, c, d, and e each represent an integer of 0 or more; and
a cation represented by a general formula (2):

$$R_s\text{-LH}^\oplus \quad (2)$$

where L represents one kind of an element selected from the group consisting of C, Si, N, P, S, and O, Rs are identical to or different from each other, and each represent a monovalent element, functional group, or organic group, and Rs may represent elements bonded to each other, and s represents an integer of 2, 3, or 4, and includes a value determined by a valence of the element represented by L.

In a preferred embodiment, the cation is represented by a general formula (3):

(3)

where $R^1$, $R^2$, and $R^3$ are identical to or different from one another, and each represent a hydrogen element or a hydrocarbon group having 1 to 8 carbon atoms, and, when at least two of $R^1$, $R^2$, and $R^3$ each represent a hydrocarbon group, those hydrocarbon groups may be directly bonded to each other, or may be bonded to each other through at least one kind of an element selected from O, S, and N.

In the preferred embodiment, X in the general formula (1) represents C or N.

The ionic compound of the present invention includes a compound represented by a general formula (4) and having a boiling point of 250° C. or lower:

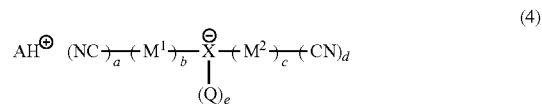
(4)

where A represents a compound containing one kind of an element selected from the group consisting of C, Si, N, P, S, and O, X represents at least one kind of an element selected from the group consisting of B, C, N, O, Al, Si, P, S, As, and Se, $M^1$ and $M^2$ are identical to or different from each other, and represent linking groups, and, when multiple $M^1$s or multiple $M^2$s are present, the multiple $M^1$s or the multiple $M^2$s may be identical to or different from each other, Q represents a monovalent element or organic group, a represents an integer of 1 or more, and b, c, d, and e each represent an integer of 0 or more.

In the preferred embodiment, A in the general formula (4) represents an amine compound.

In the preferred embodiment, X in the general formula (4) represents C or N.

The ionic compound of the present invention includes:
a cation represented by a general formula (2):

$$R_s\text{-}LH^{\oplus} \quad (2)$$

where L represents one kind of an element selected from the group consisting of C, Si, N, P, S, and O, Rs are identical to or different from each other, and each represent a monovalent element, functional group, or organic group, and Rs may represent elements bonded to each other, and s represents an integer of 2, 3, or 4, and includes a value determined by a valence of the element represented by L; and
a counter anion,
in which the ionic compound has an ionic conductivity at 25° C. of 10 mS/cm or more.

The ionic compound of the present invention includes:
an electrolyte salt represented by a general formula (5):

$$(R')_t Z^{\oplus} C^{\ominus} \quad (5)$$

where Z represents C, Si, N, P, S, or O, R' represents a halogen atom, a functional group, or an organic group, and t represents 3, 4, or 5; and
an electrolyte salt represented by a general formula (6):

$$(R'')_u YH^{\oplus} B^{\ominus} \quad (6)$$

where Y represents C, Si, N, P, S, or O, R" represents a hydrogen atom, a halogen atom, a functional group, or an organic group, and u represents 2, 3, or 4,
in which at least one of $C^-$ in the general formula (5) and $B^-$ in the general formula (6) is represented by a general formula (1):

$$(NC)_a\text{--}(M^1)_b\text{--}\underset{|(Q)_e}{\overset{\ominus}{X}}\text{--}(M^2)_c\text{--}(CN)_d \quad (1)$$

where X represents at least one kind of an element selected from the group consisting of B, C, N, O, Al, Si, P, S, As, and Se, $M^1$ and $M^2$ are identical to or different from each other, and represent linking groups, and, when multiple $M^1$s or multiple $M^2$s are present, the multiple $M^1$s or the multiple $M^2$S may be identical to or different from each other, Q represents a monovalent element or organic group, a represents an integer of 1 or more, and b, c, d, and e each represent an integer of 0 or more.

In the preferred embodiment, at least one of Z in the general formula (5) and Y in the general formula (6) represents N.

In the preferred embodiment, the cation in the general formula (6) represents a tertiary ammonium cation.

The ionic compound of the present invention includes:
an electrolyte salt represented by a general formula (7):

$$R^5\text{--}N\underset{R^6}{\overset{R^4}{\diagup}}\underset{+}{\diagdown}N\underset{R^7}{\text{--}R^8}\ D^{\ominus} \quad (7)$$

where $R^4$ represents a hydrogen atom or an organic group having 1 to 12 carbon atoms, and $R^5$ to $R^8$ each represent an organic group having 1 to 12 carbon atoms; and
an electrolyte salt represented by a general formula (6):

$$(R'')_u YH^{\oplus} B^{\ominus} \quad (6)$$

where Y represents C, Si, N, P, S, or O, R" represents a hydrogen atom, a halogen atom, a functional group, or an organic group, and u represents 2, 3, or 4.

In the preferred embodiment, the cation in the general formula (6) is represented by a general formula (3):

$$R^2\text{--}\underset{R^3}{\overset{R^1}{\underset{|}{\overset{|}{N}}}}H^{\oplus} \quad (3)$$

where $R^1$, $R^2$, and $R^3$ are identical to or different from one another, and each represent a hydrogen element or a hydrocarbon group having 1 to 8 carbon atoms, and, when at least two of $R^1$, $R^2$, and $R^3$ each represent a hydrocarbon group, those hydrocarbon groups may be directly bonded to each other, or may be bonded to each other through at least one kind of an element selected from O, S, and N.

In the preferred embodiment, at least one of $D^-$ in the general formula (7) and $B^-$ in the general formula (6) is represented by a general formula (1):

$$(NC)_a\text{--}(M^1)_b\text{--}\underset{|(Q)_e}{\overset{\ominus}{X}}\text{--}(M^2)_c\text{--}(CN)_d \quad (1)$$

where X represents at least one kind of an element selected from the group consisting of B, C, N, O, Al, Si, P, S, As, and Se, $M^1$ and $M^2$ are identical to or different from each other, and represent linking groups, and, when multiple $M^1$s or multiple $M^2$s are present, the multiple $M^1$s or the multiple $M^2$S may be identical to or different from each other, Q represents a monovalent element or organic group, a represents an integer of 1 or more, and b, c, d, and e each represent an integer of 0 or more.

According to another aspect of the present invention, there is provided an electrolyte material. The electrolyte material of the present invention contains the above ionic compound.

In the preferred embodiment, the electrolyte material further includes a matrix material.

According to another aspect of the present invention, there is provided an electrolyte solution. The electrolyte solution of the present invention contains the above ionic compound.

According to another aspect of the present invention, there is provided an electrolytic capacitor. The electrolytic capacitor of the present invention uses the above electrolytic solution.

According to the present invention, there can be provided an ionic compound which: can exert excellent basic performance such as excellent electrochemical stability including an excellent ionic conductivity; is excellent in pH stability; and can suitably find use in a variety of applications, and an electrolyte material, an electrolytic solution, and an electrolytic capacitor each containing the ionic compound.

Figure 1:
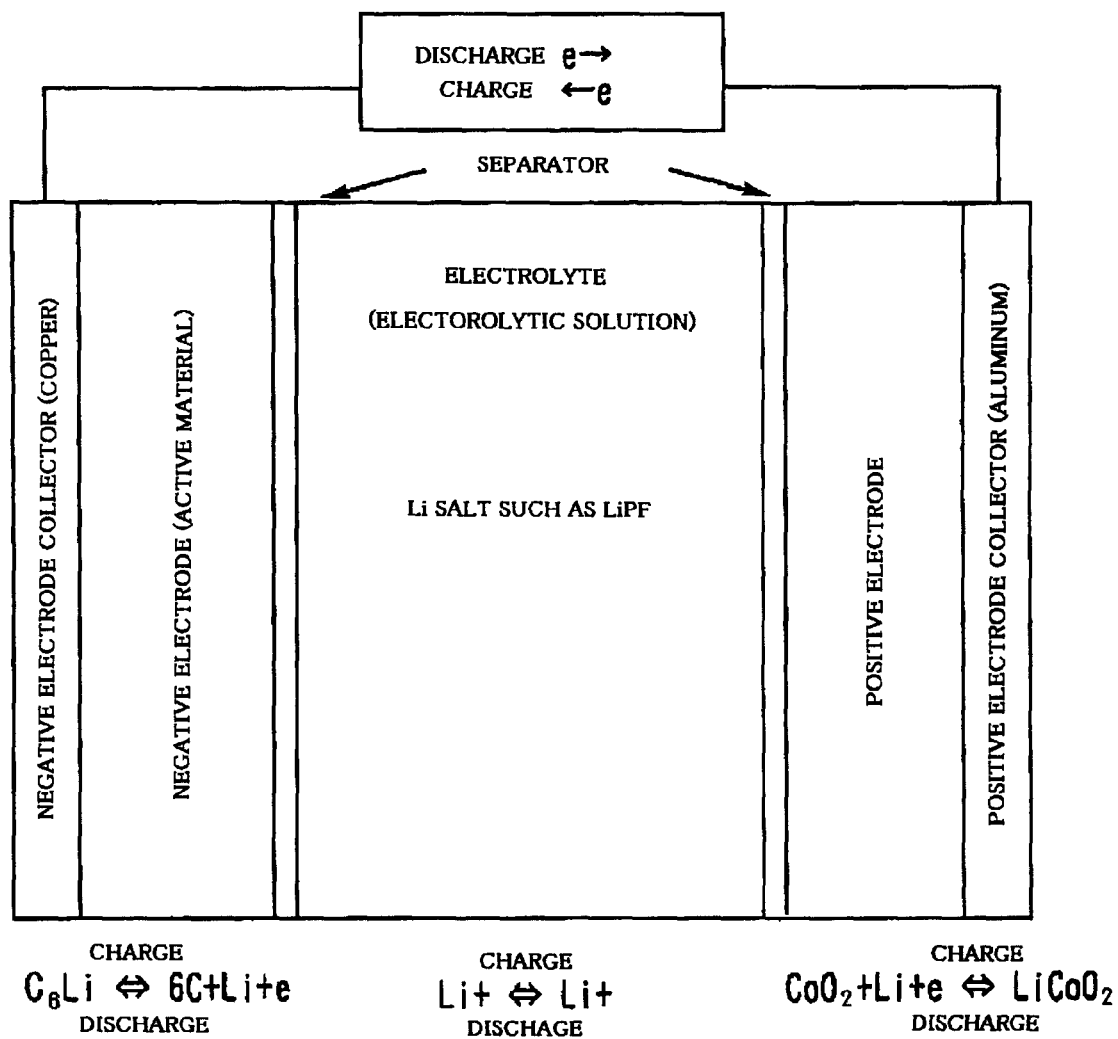
FIG. 1 is a schematic sectional view showing one shape of a lithium secondary cell.

The description of the reference numerals in the figures is as shown below.

1 anode foil
2 cathode foil
3 separator
4 anode extraction lead
5 cathode extraction lead
6 element
7 elastic sealing body
8 closed-end cylindrical exterior case
9 sealing body
10 crimping (or welding)
11 anode tab terminal
12 cathode tab terminal
13 anode terminal
14 cathode terminal
15 anode internal terminal
16 cathode internal terminal
17 device fixing agent
18 lead terminal
19 insulating plate

DETAILED DESCRIPTION OF THE PREFERRED EMBODIMENTS

Anionic compound in the specification has an anion and a cation. The ionic compound in the specification may be the form of an ionic compound-containing composition (ionic composition) containing something except the anion and the cation. The term "ionic compound" as used in the specification refers to the "ionic compound-containing composition (ionic composition)" in some cases.

The term "organic group" as used in the specification refers to a group having at least one carbon atom. That is, the term "organic group" as used in the specification may refer to a group having at least one carbon atom, the group further having any other group or atom such as: a functional group such as an amino group, an imino group, an amide group, a group having an ether bond, a group having a thioether bond, an ester group, a hydroxyl group, a carboxyl group, a carbamoyl group, a cyano group, or a sulfide group; or a halogen atom.

<<A-1. First Embodiment of Ionic Compound of the Present Invention>>

An ionic compound of the present invention uses an anion represented by the above general formula (1) as an essential ingredient, whereby the compound can be a material which: is additionally excellent in an ionic conductivity; has sufficiently suppressed corrosivity against, for example, an electrode; and is stable over time.

In the above general formula (1), X represents at least one kind of an element selected from the group consisting of B, C, N, O, Al, Si, P, S, As, and Se, and preferably represents C, N, or O, more preferably represents C or N, or still more preferably represents C. $M^1$ and $M^2$ are identical to or different from each other, and represent linking groups, and each independently represent preferably at least one kind of a linking group selected from the group consisting of —S—, —O—, —$SO_2$—, and —CO—, or more preferably —$SO_2$— or —CO—. Q represents a monovalent element or organic group, and represents preferably at least one kind of a monovalent element or organic group selected from the group consisting of: a hydrogen element; a halogen element; an alkyl group, an allyl group, and an acyl group, and a substituted derivative of any one of those groups; and $C_pF_{(2p+1-q)}H_q$, $OC_pF_{(2p+1-q)}H_q$, $SO_2C_pF_{(2p+1-q)}H_q$, $CO_2C_pF_{(2p+1-q)}H_q$, $SO_3C_6F_{5-r}H_r$, and $NO_2$ (where $1 \leq p \leq 6$, $0 < q \leq 13$, and $0 < r \leq 5$), or more preferably a fluorine element, a chlorine element, $C_pF_{(2p+1-q)}H_q$, or $SO_2C_pF_{(2p+1-q)}H_q$. a represents an integer of 1 or more, and b, c, d, and e each represent an integer of 0 or more. a, d, and e are each determined by the valence of the element X. For example, when X represents an oxygen element, a=1, d=0, and e=0, and when X represents a nitrogen element, any one of the following cases (1) to (3) is permitted: (1) a=2, d=0, and e=0, (2) a=1, d=1, and e=0, and (3) a=1, d=0, and e=1. In addition, b and c each preferably represent 0. That is, a mode in which a cyano group is directly bonded to X is preferred, and, in this case, the ionic compound does not have any group represented by each of $M^1$ and $M^2$.

In the anion represented by the above general formula (1), X preferably represents N or C, or more preferably represents C. That is, an ionic compound in which X in the above general formula (1) represents a carbon element is also a preferred embodiment of the present invention. In this case, the anion represented by the above general formula (1) is an anion represented by the following general formula (9) in which X in the general formula (1) represents C:

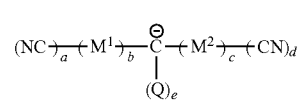 (9)

where $M^1$, $M^2$, Q, a, b, c, d, and e each have the same meaning as that described above.

The anion represented by the above general formula (1) is preferably an anion represented by the following general formula (10) in which e represents 0. The anion is more preferably a tricyanomethide anion, a dicyanoamide anion, a thioisocyanate anion, or a cyanooxy anion, or still more preferably a dicyanoamide anion or a tricyanomethide anion. This is because the any anion is free from fluorine, and is excellent in the corrosion resistance of, for example, an electrode. The anion is particularly preferably a tricyanomethide anion. An anion represented by the following general formula (11) or (12) is also preferred.

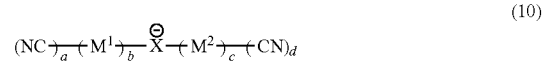 (10)

 (11)

(12)

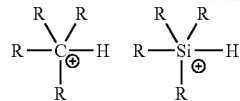

In the above ionic compound, the amount of the anion is such that the lower limit value for the content of a compound from which the anion is derived is preferably 1 weight %, more preferably 5 weight %, or still more preferably 10 weight % with respect to 100 weight % of the ionic compound. The upper limit value for the content of the compound from which the anion is derived is preferably 99.5 weight %, more preferably 95 weight %, or still more preferably 90 weight %.

In the above general formula (2), L represents one kind of an element selected from the group consisting of C, Si, N, P, S, and O, and preferably represents N, P, or S, or more preferably represents N. When L represents N, the ionic compound is chemically and electrochemically stable.

In the above general formula (2), Rs are identical to or different from each other, and each represent a monovalent element, functional group, or organic group, and Rs may represent elements bonded to each other. The above monovalent element, functional group, or organic group is preferably, for example, a hydrogen element, a fluorine element, an amino group, an imino group, an amide group, an ether group, an ester group, a hydroxyl group, a carboxyl group, a carbamoyl group, a cyano group, a sulfone group, a sulfide group, a vinyl group, a hydrocarbon group having 1 to 18 carbon atoms, or a fluorocarbon group having 1 to 18 carbon atoms. The above hydrocarbon group having 1 to 18 carbon atoms, or fluorocarbon group having 1 to 18 carbon atoms may be straight-chain, branched-chain, or cyclic, and may contain a nitrogen element, an oxygen element, or a sulfur element. In addition, the number of carbon atoms in each of those groups is preferably 1 to 18, or more preferably 1 to 8.

The above monovalent element, functional group, or organic group is more preferably a hydrogen element, a fluorine element, a cyano group, a sulfone group, a hydrocarbon group having 1 to 8 carbon atoms, a hydrocarbon group having 1 to 8 carbon atoms and containing an oxygen or nitrogen element, or a fluorocarbon group having 1 to 8 carbon atoms, or still more preferably a hydrocarbon group having 1 to 8 carbon atoms, or a saturated hydrocarbon group having 1 to 8 carbon atoms and containing an oxygen or nitrogen element. In addition, when the above monovalent element, functional group, or organic group contains a nitrogen element, the nitrogen element is preferably free from a hydrogen element (no hydrogen element is preferably bonded or coordinated to the nitrogen element).

In the above general formula (2), s represents an integer of 2, 3, or 4, and is a value determined by the valence of the element represented by L. When L represents C or Si, s represents 4, when L represents N or P, s represents 3, and when L represents S or O, s represents 2. That is, a cation represented by the above general formula (2) is preferably represented by any one of the following formulae:

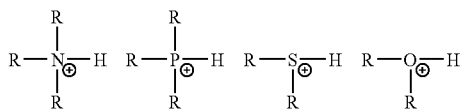

where Rs each have the same meaning as that of each of Rs in the above general formula (2). Anyone of the above-mentioned elements, functional groups, and organic groups can be suitably used as each of Rs; it is preferred that none of Rs represent a hydrogen element.

Any appropriate cation can be adopted as the cation as long as the cation satisfies the above general formula (2). Of the cations, a cation in which L represents a nitrogen element, or an onium cation is preferred.

That is, an ionic compound having an anion represented by the following general formula (1) and a cation represented by the following general formula (3) is preferred:

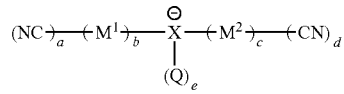
(1)

where X represents at least one kind of an element selected from the group consisting of B, C, N, O, Al, Si, P, S, As, and Se, $M^1$ and $M^2$ are identical to or different from each other, and represent linking groups, and, when multiple $M^1$s or multiple $M^2$s are present, the multiple $M^1$s or the multiple $M^2$S may be identical to or different from each other, Q represents a monovalent element or organic group, a represents an integer of 1 or more, and b, c, d, and e each represent an integer of 0 or more;

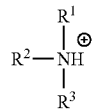
(3)

where $R^1$, $R^2$, and $R^3$ are identical to or different from one another, and each represent a hydrogen element or a hydrocarbon group having 1 to 8 carbon atoms, and, when at least two of $R^1$, $R^2$, and $R^3$ each represent a hydrocarbon group, those hydrocarbon groups may be directly bonded to each other, or may be bonded to each other through at least one kind of an element selected from O, S, and N.

As described above, X in the above general formula (1) preferably represents C or N.

The above onium cation suitably belongs to any one of the following types (I) to (IV). It should be noted that the term "onium cation" refers to an organic group having a cation of a non-metal atom or semimetal atom such as O, N, S, or P.

(I) eight kinds of heterocyclic onium cations represented by the following general formulae.

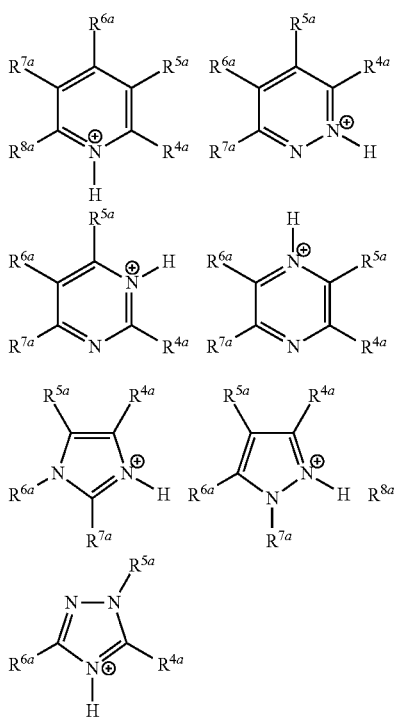

In the above general formulae, $R^{4a}$ to $R^{9a}$ are identical to or different from one another, and each represent a monovalent element, functional group, or organic group, and any two adjacent elements, functional groups, or organic groups of them may be bonded to each other, and any monovalent element, functional group, or organic group can be suitably used as each of Rs on O, N, S, and P cations; it is preferred that none of Rs represent a hydrogen element.

(II) five kinds of unsaturated onium cations represented by the following general formulae.

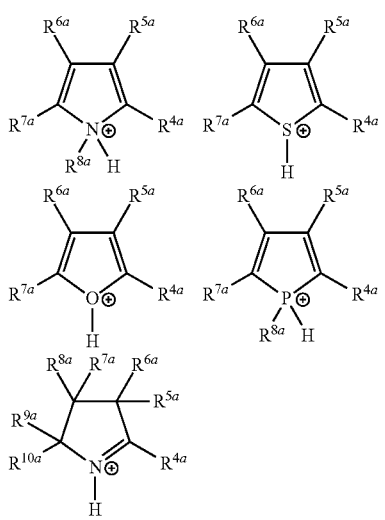

In the above general formulae, $R^{4a}$ to $R^{10a}$ are identical to or different from one another, and each represent a monovalent element, functional group, or organic group, and any two adjacent elements, functional groups, or organic groups of them may be bonded to each other, and any monovalent element, functional group, or organic group can be suitably used as each of Rs on O, N, S, and P cations; it is preferred that none of Rs represent a hydrogen element.

(III) nine kinds of saturated cyclic onium cations represented by the following general formulae.

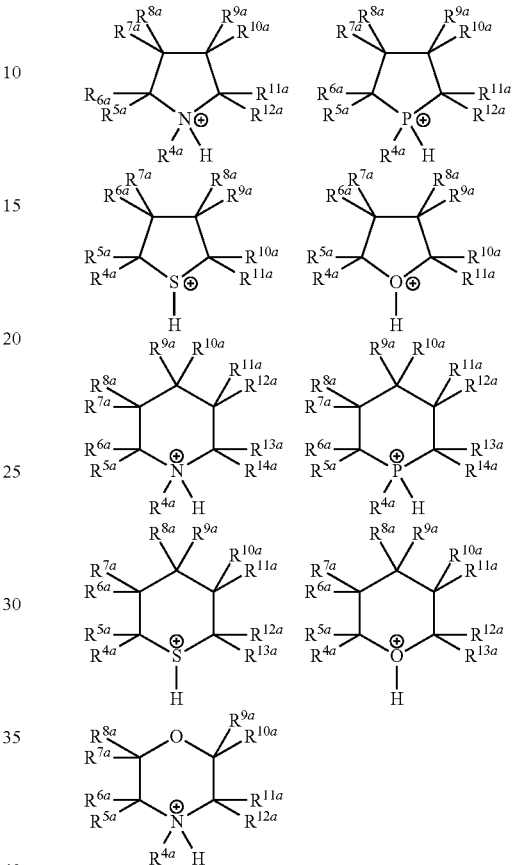

In the above general formulae, $R^{4a}$ to $R^{14a}$ are identical to or different from one another, and each represent a monovalent element, functional group, or organic group, and any two adjacent elements, functional groups, or organic groups of them may be bonded to each other, and any monovalent element, functional group, or organic group can be suitably used as each of Rs on O, N, S, and P cations; it is preferred that none of Rs represent a hydrogen element.

(IV) a chain onium cation in which one or more rs in the above general formula (2) each represent a hydrogen element, and one or more rs in the formula each represent an alkyl group having 1 to 8 carbon atoms.

Of the onium cations, an onium cation in which L in the above general formula (2) represents a nitrogen atom is more preferred.

Preferred examples of the above onium cation in which L represents a nitrogen atom include: six kinds of onium cations represented by the following general formulae; alkylammoniums such as trimethylammonium, triethylammonium, tripropylammonium, tributylammonium, dimethylethylammonium, and diethylmethylammonium; ammoniums of compounds each having two or more tertiary amines in any one of its molecules such as tetramethylethylenediamine, diazabicyclooctane, diethylenetriamine, and hexaethylenetetramine; and guanidium and an alkyl substituted product of guanidium:

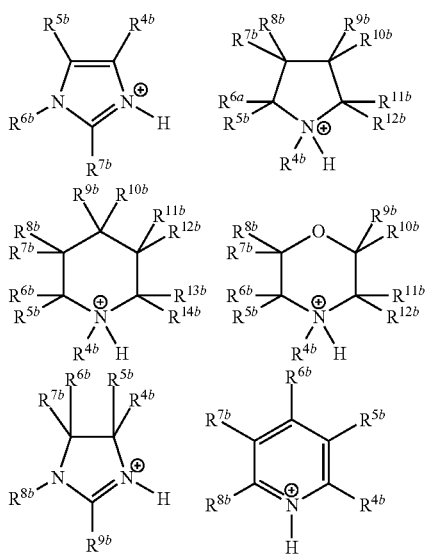

where $R^{4b}$ to $R^{14b}$ are identical to or different from one another, and each represent a monovalent element, functional group, or organic group, and any two adjacent elements, functional groups, or organic groups of them may be bonded to each other, and any monovalent element, functional group, or organic group can be suitably used as each of Rs on O, N, S, and P cations; it is preferred that none of Rs represent a hydrogen element.

Preferred examples of the above-mentioned $R^{4b}$ to $R^{14b}$ monovalent element, the functional group, or the organic group include a hydrogen element, a fluorine element, an amino group, an imino group, an amide group, an ether group, an ester group, a hydroxyl group, a carboxyl group, a carbamoyl group, a cyano group, a sulfone group, a sulfide group, a vinyl group, hydrocarbon group having 1 to 18 carbon atoms, and fluorocarbon group having 1 to 18 carbon atoms. Each of the hydrocarbon group having 1 to 18 carbon atoms and fluorocarbon group having 1 to 18 carbon atoms may have a straight-chain, a branched-chain, or a cyclic, and may contain a nitrogen element, an oxygen element, and a sulfur element. The groups preferably contain 1 to 18 carbon atoms, and more preferably 1 to 8 carbon atoms.

The above monovalent element, functional group, or organic group is more preferably a hydrogen element, a fluorine element, a cyano group, a sulfone group, a hydrocarbon group having 1 to 8 carbon atoms, a hydrocarbon group having 1 to 8 carbon atoms and containing an oxygen or nitrogen element, or a fluorocarbon group having 1 to 8 carbon atoms, or still more preferably a hydrocarbon group having 1 to 8 carbon atoms, or a saturated hydrocarbon group having 1 to 8 carbon atoms and containing an oxygen or nitrogen element. In addition, when the above monovalent element, functional group, or organic group contains a nitrogen element, the nitrogen element is preferably free from a hydrogen element (no hydrogen element is preferably bonded or coordinated to the nitrogen element).

The above ionic compound is preferably of each of the following forms (1) and (2) because of excellent heat resistance: (1) the compound uses a nitrogen cation having no conjugated double bonds as an essential ingredient; and (2) L in the above general formula (2) represents an N element, one R in the formula represents a hydrogen element, and the other Rs in the formula are identical to or different from each other, and each represent a hydrocarbon which has 1 to 8 carbon atoms and which may contain a nitrogen element, and the nitrogen element forms a tertiary amine.

The above ionic compound may contain an anion except an organic salt of an anion using the above-mentioned onium cation as an essential ingredient as long as the action and effect of the present invention are exerted.

Examples of an organic salt (organic compound) essentially containing the onium cation include halogen anions (fluoro anion, chloro anion, bromo anion, iodo anion), a borate tetrafluoride anion, a phosphate hexafluoride anion, an aluminate tetrafluoride anion, an arsenate hexafluoride anion, a sulfonylimide anion represented by the following formula (13), a sulfonylmethide anion represented by the following formula (14), and organic carboxylic acids (anions of acetic acid, trifluoroacetic acid, phthalic acid, maleic acid, benzoic acid, and the like), and further include: anions of fluorine-containing inorganic ions such as a hexafluorophosphoric acid ion, a hexafluoroarsenic acid ion, a hexafluoroantimonic acid ion, a hexafluoroniobic acid ion, and a hexafluorotantalic acid ion; carboxylic acid ions such as a hydrogen phthalate ion, a hydrogen maleate ion, a salicylic acid ion, a benzoic acid ion, and an adipic acid ion; sulfonic acid ions such as a benzenesulfonic acid ion, a toluenesulfonic acid ion, a dodecylbenzenesulfonic acid ion, a trifluoromethanesulfonic acid ion, and a perfluorobutanesulfonic acid ion; inorganic oxoacid ions such as a boric acid ion and a phosphoric acid ion; bis(trifluoromethanesulfonyl)imide ion, bis(pentafluoroethanesulfonyl)imide ion, tris(trifluoromethanesulfonyl)methide ion, perfluoroalkylfluoroborate ion, perfluoroalkylfluorophosphate ion, borodicatecholate, borodiglycholate, borodisalicylate, borotetrakis(trifluoroacetate), and tetradentate boric acid ions such as bis(oxalate)borate.

$$^{\ominus}N(SO_2R^{15})(SO_2R^{16}) \tag{13}$$

$$^{\ominus}C(SO_2R^{15})(SO_2R^{16})(SO_2R^{17}) \tag{14}$$

In the above formulae (13) and (14), $R^{15}$, $R^{16}$, and $R^{17}$ may be identical to or different from each other, and represent a perfluoroalkyl group having 1 to 4 carbon atoms which may optionally have one or two ether groups.

In the above ionic compound, the lower limit value for the amount of the above onium cation is preferably 0.5 mol, or more preferably 0.8 mol with respect to 1 mol of the above anion. In addition, the upper limit value for the amount is preferably 2.0 mol, or more preferably 1.2 mol.

The above-mentioned ionic composition may further contain an alkali metal salt and/or an alkaline earth metal salt. The an ionic composition containing an alkali metal salt and/or an alkaline earth metal salt contains the alkali metal salt and/or the alkaline earth metal salt as an electrolyte, and preferably serves as a material for ionic conductors of electrochemical devices. The an alkali metal salt preferably includes lithium salts, sodium salts, and potassium salts. The an alkaline earth metal salt preferably includes calcium salts and magnesium salts. Lithium salts are more preferred.

The above-mentioned alkali metal salt and/or alkaline earth metal salt may be an ionic substance essentially containing the above-mentioned anion or may be a compound other than the substance.

Alkali metal salts and/or alkaline earth metal salts of anion represented by the general formula (1) are preferred when the above-mentioned alkali metal salt and/or alkaline earth metal salt are/is the above-mentioned ionic compound(s) essentially containing the anion. For example, lithium salt of anion may be used as the above-mentioned alkali metal salt and/or alkaline earth metal salt. Lithium salts may be used as other alkali metal salts and/or alkaline earth metal salts. Preferred examples of the lithium salts include $LiC(CN)_3$, $LiSi(CN)_3$, $LiB(CN)_4$, $LiAl(CN)_4$, $LiP(CN)_2$, $LiP(CN)_6$, $LiAs(CN)_6$, LiOCN, and LiSCN.

Electrolyte salts showing a high dissociation constant in an electrolytic solution or a polymer solid electrolyte are preferred when the above-mentioned alkali metal salts and/or alkaline earth metal salts are compounds other than the above-mentioned ionic compound. Preferred examples thereof include alkali metal salts and alkaline earth metal salts of trifluoromethanesulfonic acid, such as $LiCF_3SO_3$, $NaCF_3SO_3$, and $KCF_3SO_3$; alkali metal salts and alkaline earth metal salts of perfluoroalkanesulfonimide, such as $LiN(CF_3SO_3)_3$ and $LiN(CF_3CF_3SO_2)_2$; alkali metal salts and alkaline earth metal salts of hexafluorophosphate, such as $LiPF_6$, $NaPF_6$, and $KPF_6$; alkali metal salts and alkaline earth metal salts of perchloric acid, such as $LiClO_4$ and $NaClO_4$; tetrafluoroborate salts such as $LiBF_4$ and $NaBF_4$; and alkali metal salts such as $LiAsF_6$, LiI, NaI, $NaAsF_6$, and KI. Of those, $LiPF_6$, $LiBF_4$, $LiAsF_6$, and alkali metal salts or alkaline earth metal salts of perfluoroalkanesulfonimide are preferred in view of solubility and ionic conductivity.

The above-mentioned ionic compounds may be solidified when containing a polymer. The a solidified composition can be preferably used as a polymer solid electrolyte.

Examples of the above-mentioned polymer include polyvinyl polymers such as polyacrylonitrile, poly(meth)acrylates, polyvinyl-based polymers such as polyvinyl chloride and polyvinylidene fluoride; polyether polymers such as polyoxymethylene, polyethylene oxide, and polypropylene oxide; polyamide polymers such as nylon 6 and nylon 66; polyester polymers such as polyethylene terephthalate; polystyrene; polyphosphazenes; polysiloxane; polysilane; polyvinylidene fluoride; polytetrafluoroethylene; polycarbonate polymers; and ionene polymers. One or more kinds of them can be preferably used.

When the above-mentioned ionic composition is used as a polymer solid electrolyte, with respect to the polymer amount in the ionic composition, it is preferred that the lower limit be 0.1% by weight and the upper limit be 5000% by weight with respect to 100% by weight of the ionic composition. When the amount is less than 0.1% by weight, the effect attributed to the solidification may be insufficiently improved. When the amount is more than 5000% by weight, the ionic conductivity may be reduced. The lower limit is more preferably 1% by weight and the upper limit is more preferably 1000% by weight.

The above ionic compound additionally increases its ionic conductivity by containing a solvent.

Any appropriate solvents capable of improving the ionic conductivity can be used as the above-mentioned solvent. Water, organic solvents, and the like are preferably used, for example. As the above-mentioned organic solvents, preferably used are compounds having: better compatibility with the above-mentioned components in the ionic composition; a large permittivity; a high solubility in the electrolyte salt; a boiling point of 60° C. or more; and a wide electrochemical stable range. Organic solvents having a low moisture content (non-aqueous solvents) are more preferred. Preferred examples of the organic solvents include ethers such as 1,2-dimethoxyethane, tetrahydrofuran, 2-methyltetrahydrofuran, crown ether, triethylene glycol methyl ether, tetraethylene glycol dimethyl ether, and dioxane; carbonates such as ethylene carbonate, propylene carbonate, diethyl carbonate, and methylethyl carbonate; chain carbonates such as dimethyl carbonate, ethylmethyl carbonate, diethyl carbonate, diphenyl carbonate, and methylphenyl carbonate; cyclic carbonates such as ethylene carbonate, propylene carbonate, ethylene 2,3-dimethylcarbonate, butylene carbonate, vinylene carbonate, and ethylene 2-vinylcarbonate; aliphatic carboxylates such as methyl formate, methyl acetate, propionic acid, methyl propionate, ethyl acetate, propyl acetate, butyl acetate, and amyl acetate; aromatic carboxylates such as methyl benzoate and ethyl benzoate; carboxylic acid esters such as γ-butyrolactone, γ-valerolactone, and δ-valerolactone; phosphates such as trimethyl phosphate, ethyldimethyl phosphate, diethylmethyl phosphate, and triethyl phosphate; nitriles such as acetonitrile, propionitrile, methoxy propionitrile, glutaronitrile, adiponitrile, and 2-methylglutaronitrile; amides such as N-methylformamide, N-ethylformamide, N,N-dimethylformamide, N,N-dimethylacetamide, N-methylpyrrolidinone, N-methylpyrrolidone, and N-vinylpyrrolidone; sulfur compounds such as dimethylsulfone, ethylmethylsulfone, diethylsulfone, sulfolane, 3-methylsulfolane, and 2,4-dimethylsulfolane; alcohols such as ethylene glycol, propylene glycol, ethylene glycol monomethyl ether, and ethylene glycol monoethyl ether; ethers such as ethylene glycol dimethyl ether, ethylene glycol diethyl ether, 1,4-dioxane, 1,3-dioxolane, tetrahydrofuran, 2-methyltetrahydrofuran, 2,6-dimethyltetrahydrofuran, and tetrahydropyran; sulfoxides such as dimethylsulfoxide, methylethyl sulfoxide, and diethylsulfoxide; aromatic nitriles such as benzonitrile and tolunitrile; nitromethane; 1,3-dimethyl-2-imidazolidinone; 1,3-dimethyl-3, 4,5,6-tetrahydro-2(1H)-pyrimidinone; and 3-methyl-2-oxazolidinone. One or more kinds of them can be preferably used. Of those, carbonates, aliphatic esters, and ethers are more preferred, and carbonates such as ethylene carbonate and propylene carbonate are still more preferred, and cyclic esters such as γ-butyrolactone and γ-valerolactone are most preferred.

The content of the above solvent is preferably 1 to 99 weight % in 100 weight % of an ionic compound-containing composition. That is, the content of the solvent is preferably 1 to 99 weight % when the total weight of the ionic compound and the solvent is defined as 100 weight %. When the content of the above solvent is less than 1 weight %, the ionic conductivity of the ionic compound is not sufficiently increased; when the content exceeds 99 weight %, the stability of the ionic compound is not sufficiently improved owing to, for example, the vaporization of the solvent. The lower limit value for the content is preferably 1.5 weight %, more preferably 20 weight %, or still more preferably 50 weight %. The upper limit value for the content is preferably 85 weight %, more preferably 75 weight %, or still more preferably 65 weight %. The solvent content preferably ranges from 50 to 85 weight %.

The above ionic compound is preferably such that the compound has a reduced volatile content, does not freeze at a temperature as low as, for example, −55° C., and is excellent in an ionic conductivity. The use of the ionic compound in an electrolytic solution can exert excellent electrical characteristics.

The above-mentioned ionic compound may contain various additives. Additives are added for the diverse purposes, and examples thereof include improvement in electrical conductivity and thermal stability, suppression of deterioration of an electrode due to hydration or dissolution, suppression of gas generation, and improvement in voltage resistant and amelioration in wettability. Examples of the additives include: nitro compounds such as p-nitrophenol, m-nitroacetophenone, and p-nitrobenzoic acid; phosphorus compounds such as dibutyl phosphate, monobutyl phosphate, dioctyl phosphate, monooctyl octylphosphonate, phosphoric acid, phosphorous acid, and nyphosphorous acid; boron acid or boron compounds such as complex compounds of boric acid with polyhydric alcohols (ethylene glycol, glycerin, mannitol, polyvinyl alcohol, or the like) or polysaccharides; nitroso compounds; urea compounds; arsenic compounds; titanium compounds; silicic acid compounds; aluminic acid compounds; nitric acid and nitrous acid compounds; benzoic acids such as 2-hydroxy-N-methylbenzoic acid and di(tri) hydroxybenzoic acid; acids such as gluconic acid, bichromic acid, sorbic acid, dicarboxylic acid, EDTA, fluorocarboxylic acid, picric acid, suberic acid, adipic acid, sebacic acid, heteropoly acid (tungstic acid, molybdic acid), gentisic acid, borodigentisic acid, salicylic acid, N-aminosalicylic acid, borodiprotocatechuic acid, borodipyrocatechol, bamonic acid, bonic acid, borodiresorcinic acid, resorcinic acid, borodiprotocachueric acid, glutamic acid, and dithiocarbamic acid, esters thereof, amides thereof and salts thereof; silane coupling agents; silicon compounds such as silica and aminosilicate; amine compounds such as triethylamine, and hexamethylenetetramine; L-amino acids; benzol; polyhydric phenol; 8-oxyqiunoline; sulfur compounds such as hydroquinone, N-methylpyrocatechol, quinoline, thioanisole, thiocresol, and thiobenzoic acid; sorbitol; and L-histidine. One or more kinds of them may be used.

Any appropriate amount can be adopted as the content of the above additive. For example, the content ranges from preferably 0.1 to 20 weight %, or more preferably 0.5 to 10 weight % with respect to 100 weight % of the ionic compound.

It is also preferred that the above-mentioned ionic compound have an impurity content of 0.1% by weight (1,000 ppm) or less in 100% by weight of the ionic compound. If the ionic compound is more than 0.1% by weight, the electrochemical stability may be insufficiently obtained. The impurity content is more preferably 0.05% by weight or less, and still more preferably 0.01% by weight or less.

The impurity does not contain water, and examples thereof include impurities which are mixed during preparation or transportation of the ionic compound. Specifically, when an ionic compound essentially containing an anion represented by the general formula (1) is produced by using a halogen compound and deriving an ionic compound, for example, the halogen compound may be mixed as an impurity. If the ionic compound is produced by using silver salt and deriving an ionic compound, the silver salt may be mixed as an impurity. Production raw materials, byproducts, and the like may also be mixed as impurities.

In the present invention, when the above-mentioned impurity content in the ionic compound is set as described above, for example, it becomes possible to sufficiently suppress deterioration of performances due to poisoning of an electrode in an electrochemical device by the halogen compound, or sufficiently suppress deterioration of performances due to influence of a silver ion, an iron ion, or the like on the ionic conductivity. The impurity content is preferably measured by the following measurement method.

(Measurement Method of Impurities)
(1) ICP (measurement of cations such as silver ion and iron ion) Instrument: ICP light emitting spectrophotometry apparatus called SPS4000 (manufactured by Seiko Instruments Inc.)
Method: A sample 0.3 g is 10-fold diluted with ion-exchanged water, and the resulting solution is measured.
(2) Ion chromatography (Measurement of anions such as nitric acid ion, bromine ion, chlorine ion, and sulfuric ion) Instrument: Ion chromatography system DX-500 (manufactured by Nippon Dionex Co., Ltd.)
Separation mode: Ion exchange
Detector: Electric conductivity detector CD-20
Column: AS4A-SC
Method: A sample 0.3 g is 100-fold diluted with ion-exchanged water, and the resulting solution is measured.

A water content in the above ionic compound is preferably 0.05 to 10 weight % in 100 weight % of the ionic compound. When the water content is less than 0.05 weight %, it becomes difficult to manage the water content in the ionic compound, and the difficulty may lead to an increase in cost. In addition, when the water content exceeds 10 weight %, the ionic compound may be unable to exert electrical stability sufficiently. The lower limit for the water content is preferably 0.1 weight %, and the upper limit for the water content is preferably 5 weight %. The lower limit is more preferably 0.5 weight %, and the upper limit is more preferably 3 weight %.

It should be noted that the water content is preferably measured by the following measurement method.
(Method of Measuring Water Content)

A sample is prepared by: mixing 0.25 g of a measurement sample and 0.75 g of dehydrated acetonitrile in a glow box having a dew point of $-80°$ C. or lower; and collecting 0.5 g of the mixed solution with a sufficiently dried TERUMO Syringe (trade name, 2.5 ml) in the glow box. After that, the water content of the sample is measured with a Karl Fischer moisture meter AQ-7 (trade name, manufactured by Hiranuma Sangyo Corporation).

Although a method of producing the above ionic compound is not particularly limited, a production method including the step of deriving an ionic substance from a compound having an anion represented by the above general formula (1) is suitable. The method can make the ionic substance suitable as a molten salt or a salt of which a solid electrolyte is constituted. The production method preferably includes the step of deriving an ionic substance from a compound having an anion with a structure represented by the above general formula (1) by using a halide or carbonate, and, for example, the following method is suitable: the method includes the step of causing a compound having an anion represented by the above general formula (1) and a halide or carbonate to react with each other, and the halide or carbonate has an onium cation or a cation using at least one kind of a metal atom selected from an alkali metal atom, an alkaline earth metal atom, a transition metal atom, and a rare earth metal atom as an essential ingredient. One or two or more kinds of those production raw materials can be used. It should be noted that the above production method may involve the use of an anion exchange resin in the present invention.

The above production method may include the step of producing a compound having an anion represented by the above general formula (1) to be used in the step of deriving an ionic substance from a compound having an anion represented by the above general formula (1). In this case, the compound having an anion represented by the above general formula (1) is preferably produced by causing the compound having an anion represented by the above general formula (1) as described above and a halide or carbonate to react with each other. With the procedure, the structure of the anion represented by the above general formula (1) in the ionic substance can be appropriately set depending on, for example, performance requested of an ionic compound. In this case, an anion represented by the above general formula (1) possessed by the compound having the anion as a production raw material in the step of producing a compound having the anion and the anion represented by the above general formula (1) in the ionic substance are not identical to each other. In addition, another preferred production method includes the step of causing a compound such as a tertiary amine and an acid type compound represented by the above general formula (1) to react with each other.

One form of a reaction formula in the step of deriving an ionic substance from a compound having an anion represented by the above general formula (1) in the above step is shown in the following formula.

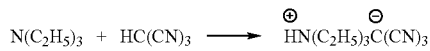

$$N(C_2H_5)_3 + HC(CN)_3 \longrightarrow \overset{\oplus}{H}N(C_2H_5)_3 \overset{\ominus}{C}(CN)_3$$

In the above-mentioned step, when the molar number of the compound containing the anion represented by the general formula (1) is referred to as x and the molar number of the halide is referred to as y, the molar ratio (x/y) in the reaction is preferably 100/1 to 0.1/1. When the compound containing the anion is less than 0.1, the halide is excessive, which may fail to generate a product effectively. In addition, the halogen may be mixed in the ionic composition and thereby electrodes and the like may be poisoned. When the compound containing the anion is more than 100, the compound is excess and therefore improvement in yield may not be expected anymore. In addition, the metal ion is mixed in the ionic composition and thereby performances of electrochemical devices may be reduced. The molar ratio is more preferably 10/1 to 0.5/1.

The reaction conditions in the above-mentioned step may be appropriately set depending on the production raw materials, other reaction conditions, and the like. The reaction temperature is preferably −20 to 200° C., and more preferably 0 to 100° C., and still more preferably 10 to 60° C. The reaction pressure is preferably $1 \times 10^2$ to $1 \times 10^8$ Pa, and more preferably $1 \times 10^3$ to $1 \times 10^7$ Pa, and still more preferably $1 \times 10^4$ to $1 \times 10^6$ Pa. The reaction time is preferably 48 hours or less, and more preferably 24 hours or less, and still more preferably 12 hours or less.

In the above-mentioned step, a reaction solvent is usually used. Examples of the a reaction solvent include (1) aliphatic hydrocarbons such as hexane and octane; (2) alicyclic saturated hydrocarbons such as cyclohexane; (3) alicyclic unsaturated hydrocarbons such as cyclohexene; (4) aromatic hydrocarbons such as benzene, toluene, and xylene; (5) ketones such as acetone and methyl ethyl ketone; (6) esters such as methyl acetate, ethyl acetate, butyl acetate, and γ-butyrolactone; (7) halogenated hydrocarbons such as dichloroethane, chloroform, and carbon tetrachloride; (8) ethers such as diethyl ether, dioxane, and dioxolane; (9) ethers of alkylene glycols such as propylene glycol monomethyl ether acetate and diethylene glycol monomethyl ether acetate; (10) alcohols such as methyl alcohol, ethyl alcohol, butyl alcohol, isopropyl alcohol, ethylene glycol, and propylene glycol monomethyl ether; (11) amides such as dimethylformamide and N-methylpyrrolidone; (12) sulfonic acid esters such as dimethyl sulfoxide; (13) carbonates such as dimethyl carbonate and diethyl carbonate; (14) alicyclic carbonates such as ethylene carbonate and propylene carbonate; (15) nitriles such as acetonitrile; and (16) water. One or more kinds of them may be used. Of those, preferred are the solvents (5), (6), (10), (11), (12), (13), (14), (15), and (16). More preferred are the solvents (5), (6), (10), (14), (15), and (16).

In the above-mentioned production method of the ionic compound, treatments such as filtration of precipitates and the like, removal of the solvent, dehydration, and drying under reduced pressure may be performed after the above-mentioned steps. For example, the ionic compound may be obtained as follows. The generated precipitates are filtered to obtain a solvent containing the ionic substance, the solvent is removed under a vacuum condition or the like, the obtained substance is washed by dissolving in a solvent such as dichloromethane, the washed substance is dehydrated by adding a substance having a dehydration effect such as $MgSO_4$ thereto, and the dehydrated substance is dried under reduced pressure after removal of the solvent. The number of times of the washing with the solvent may be appropriately set. Preferred examples of the solvent include: ketones such as chloroform, tetrahydrofuran, and acetone; ethers such as ethylene glycol dimethyl ether; acetonitrile; and water, as well as dichloromethane. Preferred examples of the substance having a dehydration effect include molecular sieve, $CaCl_2$, CaO, $CaSO_4$, $K_2CO_3$, active alumina, and silica gel, as well as $MgSO_4$. The addition amount of the a substance may be appropriately set depending on the kind of the product or solvent.

<<A-2. Second Embodiment of Ionic Compound of the Present Invention>>

The ionic compound of the present invention uses a cation ($AH^+$) and an anion represented in the above general formula (4) as essential ingredients, whereby the compound is additionally excellent in an ionic conductivity. In addition, the compound has a boiling point of 250° C. or lower, so the compound can be a material which: sufficiently suppresses liquid leakage; has sufficiently suppressed corrosivity against, for example, an electrode; and is stable over time. The boiling point of the compound represented by the above general formula (4) is preferably 200° C. or lower, or more preferably 150° C. or lower.

In the above general formula (4), A represents a compound containing one kind of an element selected from the group consisting of C, Si, N, P, S, and O. Examples of an element in a cation containing A as described above include C, Si, N, P, S, and O. Of those, N, P, and S are preferred, and N is more preferred. When L represents N, the ionic compound is chemically and electrochemically stable. Accordingly, an ionic compound in which A in the above general formula (4) represents an amine compound is also a preferred embodiment of the present invention.

The above cation ($AH^+$) formed of A and a hydrogen atom is preferably represented by the following general formula (2).

$$R_s\text{-}LH^{\oplus} \qquad (2)$$

One can refer to the description in the above section A-1 for R and L shown above.

The above ionic compound is preferably of each of the following forms (1) and (2) because of excellent heat resistance: (1) the compound uses a nitrogen cation having no conjugated double bonds as an essential ingredient; and (2) L in the above general formula (2) represents an N element, and the others in the formula are identical to or different from each other, and each represent a hydrocarbon which has 1 to 8 carbon atoms and which may contain a nitrogen element, and the nitrogen element forms a tertiary amine.

s shown above represents an integer of 1, 2, or 3, and is a value determined by the valence of the element represented by L. When L represents C or Si, s represents 3, when L represents N or P, s represents 2, and when L represents S or O, s represents 1. That is, a cation represented by the above general formula (2) is preferably represented by any one of the following formulae:

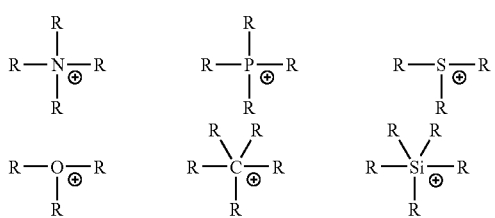

where Rs each have the same meaning as that of each of Rs in the above general formula (2), but at least one of them represents a hydrogen element.

Any appropriate cation can be adopted as the above cation as long as the cation satisfies the above general formula (2). Of the cations, a cation in which L represents a nitrogen element, or an onium cation is more preferred. One can refer to the description in the above section A-1 for the above onium cation.

The above cation (AH⁺) formed of A and a hydrogen atom is suitably represented by the following general formula (3).

Preferred examples of a monovalent element, functional group, or organic group represented by any one of $R^1$ to $R^3$ in the above general formula (3) include a hydrogen element, a fluorine element, an amino group, an imino group, an amide group, an ether group, an ester group, a hydroxyl group, a carboxyl group, a carbamoyl group, a cyano group, a sulfone group, a sulfide group, a vinyl group, a hydrocarbon group having 1 to 18 carbon atoms, and a fluorocarbon group having 1 to 18-carbon atoms. The above hydrocarbon group having 1 to 18 carbon atoms, or fluorocarbon group having 1 to 18-carbon atoms may be straight-chain, branched-chain, or cyclic, and may contain a nitrogen element, an oxygen element, or a sulfur element. In addition, the number of carbon atoms in each of those groups is preferably 1 to 18, or more preferably 1 to 8.

The above monovalent element, functional group, or organic group is more preferably a hydrogen element, a fluorine element, a cyano group, a sulfone group, a hydrocarbon group having 1 to 8 carbon atoms, a hydrocarbon group having 1 to 8 carbon atoms and containing an oxygen element, or a fluorocarbon group having 1 to 8 carbon atoms, or still more preferably a hydrocarbon group having 1 to 8 carbon atoms, or a hydrocarbon group having 1 to 8 carbon atoms and containing an oxygen or nitrogen element.

Examples of the above-mentioned A include: aliphatic amines such as methylamine, ethylamine, propylamine, butylamine, hexylamine, dimethylamine, diethylamine, dipropylamine, dibutylamine, dihexylamine, ethylmethylamine, butylmethylamine, trimethylamine, triethylamine, tripropylamine, tributylamine, dimethylethylamine, diethylmethylamine, cyclohexylamine, dicyclohexylamine, pyrrolidine, methylpyrrolidine, methylmorpholine, and methylpiperidine; aromatic amines such as aniline, dimethylaniline, nitroaniline, dimethyltoluidine, naphtylamine, pyridine, methylpyridine, quinoline, and methylpyrrol; amines containing two or more nitrogen elements in a molecule, such as tetramethylethylenediamine, diazabicyclooctane, diethylenetriamine, methylimidazole, and pyrimidine; and guanidine and an alkyl substituent thereof.

The above ionic compound may contain an anion except an organic salt of an anion using the above-mentioned onium cation as an essential ingredient as long as the action and effect of the present invention are exerted.

One can refer to the description in the above section A-1 for the above organic salt using an onium cation as an essential ingredient.

One can refer to the description in the above section A-1 for the amount of the above onium cation in the above ionic compound.

The anion that pairs up with the cation (AH⁺) in the above general formula (4) is preferably an anion represented by the above general formula (1). One can refer to the description in the above section A-1 for the anion represented by the above general formula (1).

One can refer to the description in the above section A-1 for the amount of the above anion in the above ionic compound.

The above ionic compound may further contain an alkali metal salt and/or an alkaline earth metal salt. One can refer to the description in the above section A-1 for the embodiment.

The above ionic compound solidifies by containing a polymer, whereby the compound can be suitably used as a polymer solid electrolyte. The above ionic compound additionally increases its ionic conductivity by containing a solvent.

One can refer to the description in the above section A-1 for the above polymer, the amount of the polymer when the above ionic compound is a polymer solid electrolyte, and the above solvent.

The above ionic compound is preferably such that the compound has a reduced volatile content, does not freeze at a temperature as low as, for example, −55° C., and is excellent in an ionic conductivity. The use of the ionic compound in, for example, an electrolytic solution can exert excellent electrical characteristics.

Various additives may be incorporated into the above ionic compound. One can refer to the description in the above section A-1 for the embodiment.

One can refer to the description in the above section A-1 for an impurity in the above ionic compound.

One can refer to the description in the above section A-1 for the water content in the above ionic compound.

One can refer to the description in the above section A-1 for a method of producing the above ionic compound.

<<A-3. Third Embodiment of Ionic Compound of the Present Invention>>

The ionic compound of the present invention has a cation represented by the above general formula (2) and a counter anion, and has an ionic conductivity at 25° C. of 10 mS/cm or more.

A conventional tertiary salt has a structure that is hard to dissociate as compared to that of a quaternary salt, though the tertiary salt does not cause a problem referred to as liquid leakage from a cathode portion when used in the electrolytic solution of a capacitor. Accordingly, the conventional tertiary salt could not achieve an ionic conductivity (25° C.) of 10 mS/cm or more. In the present invention, the object was achieved by designing and optimizing an anion excellent in degree of dissociation.

One can refer to the description in the above section A-1 for the cation represented by the above general formula (2).

Any appropriate anion can be adopted as the above counter anion. Preferred examples of the anion include the anion represented by the general formula (1) described in the above section A-1 and any other anion described in the above section A-1.

The above ionic conductivity at 25° C., which is 10 mS/cm or more, is preferably 15 mS/cm or more, more preferably 20 mS/cm or more, or still more preferably 25 mS/cm or more. When the above ionic conductivity at 25° C. is less than 10 mS/cm, the ionic compound cannot exert an excellent ionic conductivity, so it may be unable to provide an ionic compound that can suitably find use in a variety of applications.

The above ionic compound preferably contains a cation (AH$^+$) represented in the general formula (4) shown in the above section A-2 in terms of, for example, the suppression of liquid leakage and the suppression of the corrosion of an electrode.

<<A-4. Fourth Embodiment of Ionic Compound of the Present Invention>>

The ionic compound of the present invention contains an electrolyte salt represented by the above general formula (5) and an electrolyte salt represented by the above general formula (6), and at least one of C$^-$ in the general formula (5) and B$^-$ in the general formula (6) is represented by the above general formula (1).

Z in the above general formula (5) represents C, Si, N, P, S, or O. R's in the above general formula (5) each represent a halogen atom, a functional group, or an organic group. R's may be identical to or different from each other. R's may be bonded to each other. t represents 3, 4, or 5. It should be noted that t is a value determined by the valence of X described above.

Preferred specific examples of a cation in the above general formula (5) include onium cations represented by the following general formulae (15).

(15)

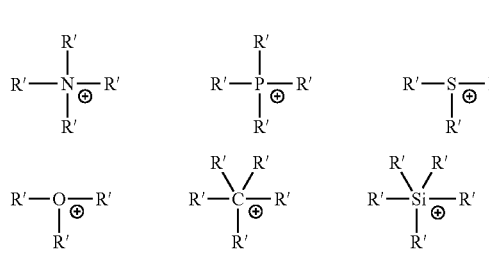

Of the above onium cations, (I) a heterocyclic onium cation represented by any one of the following general formulae:

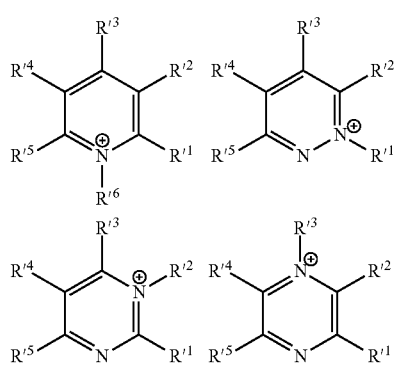

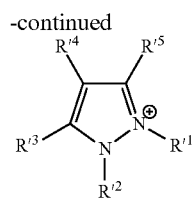

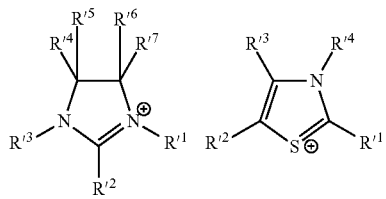

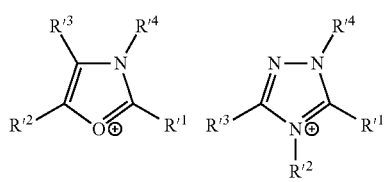

where $R'^1$ to $R'^7$ each represent a hydrogen atom, a halogen atom, a functional group, a hydrocarbon group, or a substituted hydrocarbon group, $R'^1$ to $R'^7$ may be identical to or different from one another, and any two adjacent atoms or groups of $R'^1$ to $R'^7$ may be bonded to each other, (II) an unsaturated onium cation represented by any one of the following general formulae:

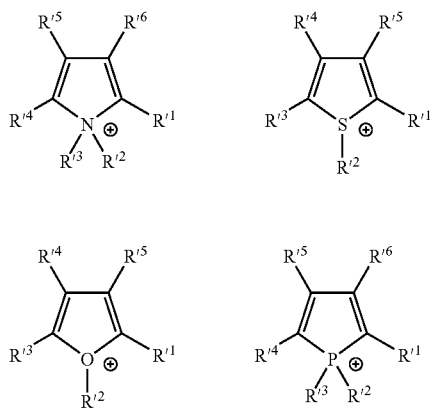

where $R'^1$ to $R'^8$ each represent a hydrogen atom, a halogen atom, a functional group, a hydrocarbon group, or a substituted hydrocarbon group, $R'^1$ to $R'^8$ may be identical to or different from one another, and any two adjacent atoms or groups of $R'^1$ to $R'^8$ may be bonded to each other, (III) a saturated cyclic onium cation represented by any one of the following general formulae:

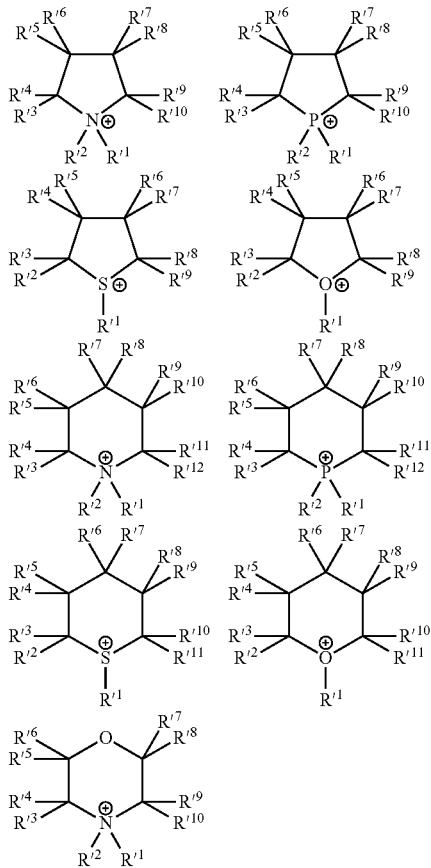

where $R'^1$ to $R'^{12}$ each represent a hydrogen atom, a halogen atom, a functional group, a hydrocarbon group, or a substituted hydrocarbon group, $R'^1$ to $R'^{12}$ may be identical to or different from one another, and any two adjacent atoms or groups of $R'^1$ to $R'^{12}$ may be bonded to each other, or (IV) a chain onium cation represented by any one of the following general formulae:

(15)

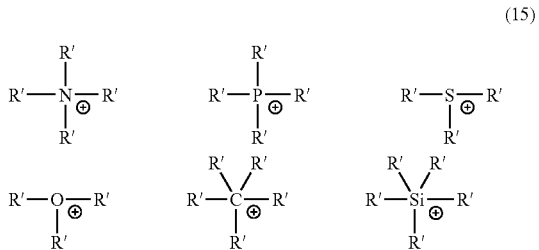

where R' represents an alkyl group having 1 to 8 carbon atoms is more preferred.

Preferred examples of $R'^1$ to $R'^{12}$ in the above formulae (1) to (III) include a hydrogen atom, a fluorine atom, an amino group, an imino group, an amide group, an ether group, an ester group, a hydroxyl group, a carboxyl group, a carbamoyl group, a cyano group, a sulfone group, a sulfide group, and a straight-chain, branched-chain, or cyclic hydrocarbon or fluorocarbon group which has 1 to 18 carbon atoms and which may contain a nitrogen atom, an oxygen atom, a sulfur atom, or the like. Of those, a hydrogen atom, a fluorine atom, a cyano group, a sulfone group, or a hydrocarbon or fluorocarbon group having 1 to 8 carbon atoms is more preferred.

Of the above onium cations, an onium cation in which Z in the above general formula (5) represents N is particularly preferred, and, for example, an onium cation represented by any one of the following general formulae, or a chain onium cation such as triethylmethylammonium, dimethylethylpropylammonium, diethylmethylmethoxyethylammonium, trimethylpropylammonium, trimethylbutylammonium, or trimethylhexylammonium is most preferred.

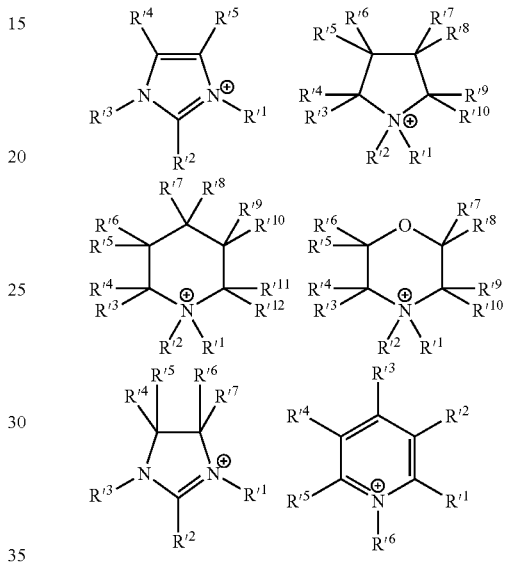

Y in the above general formula (6) represents C, Si, N, P, S, or O or preferably represents N. R''s in the above general formula (6) each represent a hydrogen atom, a halogen atom, a functional group, or an organic group. R''s may be identical to or different from each other. R''s may be bonded to each other. u represents 2, 3, or 4. It should be noted that u is a value determined by the valence of Y.

Preferred examples of the cation in the general formula (6) include: a cation represented by any one of the above-mentioned (I) to (III) (a cation in which R' in the general formula (15) is replaced with R''); an alkylammonium cation such as methylammonium, ethylammonium, propylammonium, butylammonium, hexylammonium, dimethylammonium, diethylammonium, dipropylammonium, dibutylammonium, dihexylammonium, ethylmethylammonium, butylmethylaminetrimethylammonium, trimethylammonium, triethylammonium, tripropylammonium, tributylammonium, dimethylethylammonium, and diethylmethylammonium; an ammonium cation containing two or more tertiary amines in a molecule, such as trimethylethylene diamine, diazabicycloocatane, diethylene triamine, and hexaethylene tetramine; and guanidium and an alkyl substituent thereof. Of those, preferable is a tertiary ammonium cations such as trimethylammonium, triethylammonium, tripropylammonium, tributylammonium, dimethylethylammonium, and diethylmethylammonium.

At least one of C⁻ in the above general formula (5) and B⁻ in the above general formula (6) is represented by the above general formula (1). With the constitution, the ionic compound can achieve an excellent ionic conductivity, and can be excellent in pH stability.

One can refer to the description in the above section A-1 for the anion represented by the above general formula (1).

At least one of C⁻ in the above general formula (5) and B⁻ in the above general formula (6) can be an anion except the anion represented by the above general formula (1). Specific examples of the anion include: a dicarboxylic acid anion (monoanion or dianion) of, for example, phthalic acid or maleic acid; a sulfate anion such as a methylsulfate or an ethylsulfate; a fluorine-containing inorganic ion such as a hexafluorophosphoric acid ion, a hexafluoroarsenic acid ion, a hexafluoroantimonic acid ion, a hexafluoroniobic acid ion, or a hexafluorotantalic acid ion; a carboxylic acid ion such as a salicylic acid ion, a benzoic acid ion, or an adipic acid ion; a sulfonic acid ion such as a benzenesulfonic acid ion, a toluenesulfonic acid ion, a dodecylbenzenesulfonic acid ion, a trifluoromethanesulfonic acid ion, or a perfluorobutanesulfonic acid ion; an inorganic oxo acid ion such as a boric acid ion or a phosphoric acid ion; an imide ion such as a bis(trifluoromethanesulfonyl)imide ion (TFSI) or a bis(pentafluoroethanesulfonyl)imide ion; a methide ion such as a tris(trifluoromethanesulfonyl)methide ion; a boron-based ion such as a tetrafluoroboric acid anion, a perfluoroalkylfluoroborate ion, a borodicatecholate, a borodiglycolate, a borodisalicylate, a borotetrakis(trifluoroacetate), or a bis(oxalato) borate; and a phosphate ion such as a perfluoroalkylfluorophosphate ion.

The above ionic compound can contain an alkali metal salt and/or an alkaline earth metal salt. The compound can be particularly suitable for an electrolytic solution for a cell by containing any the metal salt. A lithium salt, a sodium salt, or a potassium salt is a suitable alkali metal salt. A calcium salt or a magnesium salt is a suitable alkaline earth metal salt. A lithium salt is particularly preferably used in, for example, the case where the compound is used in a lithium secondary cell to be described later.

Any appropriate anion can be adopted as an anion of at least one of the above alkali metal salt and the above alkaline earth metal salt. Therefore, the anion represented by the above general formula (1) is permitted, and an anion except the anion is also permitted. One can refer to the description in the above section A-1 for specific examples of the anion.

The above ionic compound can contain any other electrolyte salt. Specific examples of the suitable salt include: a quaternary ammonium salt of perchloric acid such as tetraethylammonium perchlorate; a quaternary ammonium salt of tetrafluoroboric acid such as $(C_2H_5)_4NBF_4$; a quaternary ammonium salt such as $(C_2H_5)_4NPF_6$; and a quaternary phosphonium salt such as $(CH_3)_4P.BF_4$ or $(C_2H_5)_4P.BF_4$. Of those, a quaternary ammonium salt is more suitable in terms of solubility and an ionic conductivity.

<<A-5. Fifth Embodiment of Ionic Compound of the Present Invention>>

The ionic compound of the present invention contains an electrolyte salt represented by the above general formula (7) and an electrolyte salt represented by the above general formula (6). With the constitution, the ionic compound can achieve an excellent ionic conductivity, and can be excellent in pH stability.

$R^4$ in the above general formula (7) represents a hydrogen atom or an organic group having 1 to 12 carbon atoms. $R^5$ to $R^8$ in the above general formula (7) each represent an organic group having 1 to 12 carbon atoms. $R^4$ to $R^8$ may be partly or entirely bonded to each other to form a ring.

When $R^4$ in the above general formula (7) does not form a ring with any one of $R^5$ to $R^8$, examples of $R^4$ include a straight-chain aliphatic hydrocarbon group, a branched-chain aliphatic hydrocarbon group, a cyclic hydrocarbon group, and an aromatic hydrocarbon group. Examples of the straight-chain aliphatic hydrocarbon group include a methyl group, an ethyl group, an n-propyl group, an n-butyl group, an n-pentyl group, an n-hexyl group, an n-decyl group, an n-octadecenyl group, an n-eicosyl group, a hydroxymethyl group, a 1-hydroxyethyl group, and a 2-hydroxyethyl group. Examples of the branched-chain aliphatic hydrocarbon group include an iso-propyl group, a 2-methylpropyl group, a 1-methylpropyl group, a 1-methylbutyl group, a 2-methylbutyl group, a 3-methylbutyl group, a 1-ethylpropyl group, a 2-ethylpropyl group, a 1-methylpentyl group, a 2-methylpentyl group, a 3-methylpentyl group, a 4-methylpentyl group, a 1-ethylbutyl group, a 2-ethylbutyl group, a 3-ethylbutyl group, a 4-ethylbutyl group, a 2-ethylhexyl group, a 1,2-dimethylbutyl group, a 1,3-dimethylbutyl group, a 2,3-dimethylbutyl group, a 2-ethyl-n-octyl group, a 2-ethyl-n-hexadecenyl group, a 2-ethyl-n-octadecenyl group, a 2-hydroxy-iso-propyl group, and a 1-hydroxy-2-methylpropyl group. Examples of the cyclic hydrocarbon group include a cyclohexyl group, a 1-methylhexyl group, a 2-methylhexyl group, a 3-methylhexyl group, a 4-methylhexyl group, a 1-hydroxyhexyl group, 2-hydroxyhexyl group, 3-hydroxyhexyl group, and 4-hydroxyhexyl group. Examples of the aromatic hydrocarbon group include a phenyl group, a tolyl group, and a benzyl group. $R^4$ is preferably a hydrogen atom, a straight-chain aliphatic hydrocarbon group, or an aromatic hydrocarbon group, more preferably a hydrogen atom, a methyl group, an ethyl group, an n-butyl group, a phenyl group, or a benzyl group, and particularly preferably a hydrogen atom or a methyl group.

When none of $R^5$ to $R^8$ in the above general formula (7) forms a ring, examples of $R^5$ to $R^8$ include a straight-chain aliphatic hydrocarbon group, a branched-chain aliphatic hydrocarbon group, a cyclic hydrocarbon group, and an aromatic hydrocarbon group. Examples of the straight-chain aliphatic hydrocarbon group include a methyl group, an ethyl group, an n-propyl group, an n-butyl group, an n-pentyl group, an n-hexyl group, an n-decyl group, an aminomethyl group, an aminoethyl group, a nitromethyl group, a nitroethyl group, a cyanomethyl group, a cyanoethyl group, a carboxymethyl group, a carboxyethyl group, a methoxymethyl group, a methoxyethyl group, a formylmethyl group, and a formylethyl group. Examples of the branched-chain aliphatic hydrocarbon group include an iso-propyl group, a 2-methylpropyl group, a 1-methylpropyl group, a 1-methylbutyl group, a 2-methylbutyl group, a 3-methylbutyl group, a 1-ethylpropyl group, a 2-ethylpropyl group, a 1-methylpentyl group, a 2-methylpentyl group, a 3-methylpentyl group, a 4-methylpentyl group, a 1-ethylbutyl group, a 2-ethylbutyl group, a 3-ethylbutyl group, a 4-ethylbutyl group, a 1,2-dimethylbutyl group, a 1,3-dimethylbutyl group, a 2,3-dimethylbutyl group, a 2-ethyl-n-octyl group, a 2-amino-iso-propyl group, a 1-amino-2-methylpropyl group, a 2-nitro-iso-propyl group, a 1-nitro-2-methylpropyl group, a 2-cyano-iso-propyl group, a 1-cyano-2-methylpropyl group, a 2-carboxy-iso-propyl group, a 1-carboxy-2-methylpropyl group, a 2-methoxy-iso-propyl group, a 1-methoxy-2-methylpropyl group, a 2-formyl-iso-propyl group, and a 1-formyl-2-methylpropyl group. Examples of the cyclic aliphatic hydrocarbon group include a cyclohexyl group, a 1-methyl-hexyl group, a 2-methylhexyl group, a 3-methylhexyl group, a 4-methylhexyl group, a 1-aminohexyl group, a 2-aminohexyl group, a 3-aminohexyl group, a 4-aminohexyl group, a 1-cyanohexyl group, a 2-cyanohexyl group, a 3-cyanohexyl group, a 4-cyanohexyl group, a 1-carboxyhexyl group, a 2-carboxyhexyl group, a 3-carboxyhexyl group, a 4-carboxyhexyl group, a 1-methoxyhexyl group, a 2-methoxyhexyl group, a 3-methoxyhexyl group, a 4-methoxyhexyl group, a 1-formylhexyl group, a 2-formylhexyl group, a 3-formylhexyl group, and a 4-formylhexyl group. Examples of the aromatic aliphatic hydrocarbon group include a phenyl group, a tolyl group, and a benzyl group. Of those, a straight-chain aliphatic hydrocarbon group is preferred, a methyl group, a methoxyethyl group, or an ethyl group is more preferred, and a methyl group or an ethyl group is particularly preferred.

When $R^4$, $R^5$, $R^6$, $R^7$, and $R^8$ in the above general formula (7) are partly or entirely bonded to each other to form a ring or the like, examples of the structure include an alkylene group, an arylene group, and an alkenylene group. Examples of the alkylene group include a methylene group, an ethylene group, an n-propylene group, an iso-propylene group, an n-butylene group, a 1,2-dimethylethylene group, an n-pentylene group, and an n-hexylene group. An example of the arylene group is a phenylene group. Examples of the alkenylene group include an ethylenylene group, an n-propynylene group, an iso-propynylene group, an n-butylenylene group, and a 1,2-dimethylethylenylene group. Of those, an alkylene group or an alkenylene group is preferred, and an ethylene group, an iso-propylene group, a 1,2-dimethylethylene group, an ethylenylene group, an iso-propynylene group, oral, 2-dimethylethylenylene group is more preferred.

It is preferred that $R^4$, $R^5$, $R^6$, $R^7$, and $R^8$ in the above general formula (7) be partly or entirely bonded to each other to form a ring. Examples of the ring structure include an imidazoline ring, an imidazole ring, and a tetrahydropyrimidine ring. Of those, an imidazoline ring or an imidazole ring is preferred, and an imidazole ring is more preferred.

Examples of the cation in the above general formula (7) include: a imidazolinium cation such as 1,2,3-trimethylimidazolinium, 1,2,3,4-tetramethylimidazolinium, 1,3,4-trimethyl-2-ethylimidazolinium, 1,3-dimethyl-2,4-diethylimidazolinium, 1,2-dimethyl-3,4-diethylimidazolinium, 1-methyl-2,3,4-triethylimidazolinium, 1,2,3,4-tetraethylimidazolinium, 1,3-dimethyl-2-ethylimidazolinium, 1-ethyl-2,3-dimethylimidazolinium, 1,2,3-triethylimidazolinium, 1,1-dimethyl-2-heptylimidazolinium, 1,1-dimethyl-2-(2'-heptyl)imidazolinium, 1,1-dimethyl-2-(3'-heptyl)imidazolinium, 1,1-dimethyl-2-(4'-heptyl)imidazolinium, 1,1-dimethyl-2-dodecylimidazolinium, 1,1-dimethylimidazolinium, 1,1,2-trimethylimidazolinium, 1,1,2,4-tetramethylimidazolinium, 1,1,2,5-tetramethylimidazolinium, and 1,1,2,4,5-pentamethylimidazolinium; a imidazolium cation such as 1,3-dimethylimidazolium, 1-ethyl-3-methylimidazolium, 1,3-diethylimidazolium, 1,2,3-trimethylimidazolium, 1,2,3,4-tetramethylimidazolium, 1,3,4-trimethyl-2-ethylimidazolium, 1,3-dimethyl-2,4-diethylimidazolium, 1,2-dimethyl-3,4-diethylimidazolium, 1-methyl-2,3,4-triethylimidazolium, 1,2,3,4-tetraethylimidazolium, 1,3-dimethyl-2-ethylimidazolium, 1-ethyl-2,3-dimethylimidazolium, 1,2,3-triethylimidazolium, 1,1-dimethyl-2-heptylimidazolium, 1,1-dimethyl-2-(2'-heptyl)imidazolium, 1,1-dimethyl-2-(3'-heptyl)imidazolium, 1,1-dimethyl-2-(4'-heptyl)imidazolium, 1,1-dimethyl-2-dodecylimidazolium, 1,1-dimethylimidazolium, 1,1,2-trimethylimidazolium, 1,1,2,4-tetramethylimidazolium, 1,1,2,5-tetramethylimidazolium, and 1,1,2,4,5-pentamethylimidazolium; tetrahydropyridium cations such as 1,3-dimethyl-1,4,5,6-tetrahydropyrimidium, 1,2,3-trimethyl-1,4,5,6-tetrahydropyrimidium, 1,2,3,4-tetramethyl-1,4,5,6-tetrahydropyrimidium, 1,2,3,5-tetramethyl-1,4,5,6-tetrahydropyrimidium, 8-methyl-1,8-diazabicyclo[5.4.0]-7-undecenium, 5-methyl-1,5-diazabicyclo[4.3.0]-5-nonenium, 8-ethyl-1,8-diazabicyclo[5.4.0]-7-undecenium, and 5-ethyl-1,5-diazabicyclo[4.3.0]-5-nonenium. Of those, imidazolium cations are preferred. More preferred are 1-ethyl-3-methylimidazolium, 1,3-dimethylimidazolium, 1,3-diethylimidazolium, 1,2,3-trimethylimidazolium, 1-ethyl-2,3-dimethylimidazolium, and 1,2,3,4-tetramethylimidazolium, particularly preferred are 1-ethyl-3-methylimidazolium, 1,2,3-trimethylimidazolium, 1-ethyl-2,3-dimethylimidazolium, and most preferred are 1-ethyl-3-methylimidazolium and 1,2,3-trimethylimidazolium.

One can refer to the description in the above section A-4 for a cation represented in the above general formula (6).

The cation in the above general formula (6) is preferably a cation represented by the above general formula (3).

In the above general formula (3), $R^1$, $R^2$, and $R^3$ are identical to or different from one another, and each represent a hydrogen element or a hydrocarbon group having 1 to 8 carbon atoms. When at least two of $R^1$, $R^2$, and $R^3$ each represent a hydrocarbon group, those hydrocarbon groups may be directly bonded to each other, or may be bonded to each other through at least one kind of an element selected from O, S, and N.

Of the cations each represented by the above general formula (3), a tertiary ammonium cation such as trimethylammonium, triethylammonium, tripropylammonium, tributylammonium, dimethylethylammonium, or diethylmethylammonium is preferred.

At least one of $D^-$ in the above general formula (7) and $B^-$ in the above general formula (6) is preferably represented by the above general formula (1). With the constitution, the ionic compound can achieve an extremely excellent ionic conductivity, and can be excellent in pH stability.

One can refer to the description in the above section A-1 for the anion represented by the above general formula (1).

At least one of $D^-$ in the above general formula (7) and $B^-$ in the above general formula (6) can be an anion except the anion represented by the above general formula (1). One can refer to the description in the above section A-4 for specific examples of the anion.

The above ionic compound can contain an alkali metal salt and/or an alkaline earth metal salt. The compound can be particularly suitable for an electrolytic solution for a cell by containing the any metal salt. A lithium salt, a sodium salt, or a potassium salt is a suitable alkali metal salt. A calcium salt or a magnesium salt is a suitable alkaline earth metal salt. A lithium salt is particularly preferably used in, for example, the case where the compound is used in a lithium secondary cell to be described later.

Any appropriate anion can be adopted as an anion of at least one of the above alkali metal salt and the above alkaline earth metal salt. Therefore, the anion represented by the above general formula (1) is permitted, and an anion except the anion is also permitted. One can refer to the description in the above section A-1 for specific examples of the anion.

The above ionic compound can contain any other electrolyte salt. One can refer to the description in the above section A-4 for specific examples of the electrolyte salt.

<<B. Electrolyte Material>>

An electrolyte material of the present invention contains the ionic compound of the present invention described in each of the above sections A-1 to A-5. It should be noted that the above ionic compound, which is preferably used in an electrolyte material, can be used in a material except an electrolyte material.

The above electrolyte material preferably contains a matrix material. Preferably the electrolyte uses an organic solvent as an essential ingredient, which can be considered as a matrix material. Examples of the organic solvent include the organic solvents described in the above section A-1.

The electrolyte material of the present invention may be the very ionic compound of the present invention described in each of the above sections A-1 to A-5. In addition, the electrolyte material of the present invention may be used as it is as an electrolyte. The above electrolyte means a material for an electrolytic solution or a material for an electrolyte, and can be suitably used as at least one of (1) a solvent of which an electrolytic solution is constituted and (2) a material for an electrolyte (material for an ionic conductor), or as (3) a material for a solid electrolyte (material for an electrolyte) in the ionic conductor of an electrochemical device. For example, in the case of the above item (1), an electrolytic solution (or solid electrolyte) is constituted by incorporating a substance that shows ionic conductivity in a solvent together with the above electrolyte. In the case of the above item (2), a material for an electrolyte is constituted by incorporating the above electrolyte into a solvent. In the case of the above item (3), a solid electrolyte is obtained by using the above electrolyte as it is or by incorporating any other component into the electrolyte.

The electrolyte material of the present invention constitutes a cell having a charging/discharging mechanism such as a primary cell, a lithium (ion) secondary cell, or a fuel cell, an electrolytic solution for driving an electrolytic capacitor, or an electrochemical device such as an electrolytic capacitor, an electric double layer capacitor, a solar cell, or an electrochromic display device.

<<C. Electrolytic Solution>>

An electrolytic solution of the present invention contains the ionic compound of the present invention described in each of the above sections A-1 to A-5. The electrolytic solution can be preferably obtained by dissolving the ionic compound of the present invention described in each of the above items A-1 to A-5 in a solvent. Any appropriate solvent can be adopted as the solvent. The solvent preferably contains an organic solvent. This is because the ionic conductivity of the electrolytic solution can be additionally increased. One can refer to the description in the above section A-1 for specific examples of the organic solvent.

Upon preparation of the above electrolytic solution, the loading of the electrolyte salt represented by the above general formula (5) and the electrolyte salt represented by the above general formula (6), or the loading of the electrolyte salt represented by the above general formula (7) and the electrolyte salt represented by the above general formula (6) can be set to any appropriate value depending on purposes. The loading is preferably 1 to 900 parts by weight, more preferably 10 to 400 parts by weight, or particularly preferably 30 to 100 parts by weight with respect to 100 parts by weight of the above solvent. Causing the loading of the electrolyte salts to fall within the range can achieve an excellent ionic conductivity, and, further, can suppress the precipitation of any electrolyte salt.

A compounding ratio between the electrolyte salt represented by the above general formula (5) and the electrolyte salt represented by the above general formula (6), or a compounding ratio between the electrolyte salt represented by the above general formula (7) and the electrolyte salt represented by the above general formula (6) can be set to any appropriate value. The ratio is preferably 95:5 to 5:95, more preferably 90:10 to 50:50, or particularly preferably 90:10 to 55:45. It should be noted that the ratio is a weight ratio.

The electrolytic solution of the present invention can contain water. A water content in the electrolytic solution is preferably 0.01 to 10 weight %, more preferably 0.01 to 5 weight %, or particularly preferably 0.01 to 2 weight %. Causing the water content to fall within the range can stabilize the voltage resistance, heat resistance, and lifetime of an electrochemical device, and, further, can provide excellent chemical conversion property upon repair of an anodic oxide film.

The electrolyte solution of the present invention can contain any other component in addition to the foregoing. Examples of the other component include an inorganic oxide fine particle and an additive.

The above inorganic oxide fine particle is preferably incapable of conducting electrons and electrochemically stable. The fine particle more preferably has ionic conductivity. Examples of the inorganic oxide fine particle include ceramic fine particles each made of, for example, $\alpha$, $\beta$, $\gamma$-alumina, silica, titania, zirconia, magnesia, barium titanate, or hydrotalcite.

An appropriate additive can be adopted as the above additive depending on purposes. Examples of an object of the addition of the additive include an increase in electric conductivity, an improvement in heat stability, the suppression of the deterioration of an electrode due to hydration or dissolution, the suppression of the generation of a gas, an increase in withstand voltage, and an improvement in wettability. Examples of the additive include: nitro compounds such as p-nitrophenol, m-nitroacetophenone, and p-nitrobenzoic acid; phosphorus compounds such as dibutyl phosphate, monobutyl phosphate, dioctyl phosphate, monooctyl octylphosphonate, and phosphoric acid; boron compounds such as boric acid and a complex compound of boric acid and a polyhydric alcohol (such as ethylene glycol, glycerin, mannitol, or polyvinyl alcohol) or a polysaccharide; nitroso compounds; urea compounds; arsenic compounds; titanium compounds; silicate compounds; aluminate compounds; nitrate and nitrite compounds; benzoic acids such as 2-hydroxy-N-methylbenzoic acid and di(tri)hydroxybenzoic acid; acids such as gluconic acid, dichromic acid, sorbic acid, a dicarboxylic acid, EDTA, a fluorocarboxylic acid, picric acid, suberic acid, adipic acid, sebacic acid, a heteropolyacid (such as tungstic acid or molybdic acid), gentisic acid, borodigentisic acid, salicylic acid, N-aminosalicylic acid, borodiprotocatectic acid, borodipyrrocatechol, bamonic acid, bonic acid, borodiresorcil acid, resorcil acid, borodiprotocacuel acid, glutaric acid, and dithiocarbamic acid, and esters, amides, and salts of the acids; silane coupling agents; silicon compounds such as silica and aminosilicate; amine compounds such as triethylamine and hexamethylenetetramine; L-amino acids; benzol; polyhydric phenols; 8-oxyquinoline; hydroquinone; N-methylpyrrocatechol; quinoline; sulfur compounds such as thioanisole, thiocresol, and thiobenzoic acid; sorbitol; and L-histidine.

The electrolytic solution of the present invention has an ionic conductivity of typically 10 mS/cm or more, preferably 15 mS/cm or more, or more preferably 20 mS/cm or more. It should be noted that the term "ionic conductivity" as used in the specification refers to a value measured at 25° C.

The electrolytic solution of the present invention shows a pH variation of typically 6 or less, preferably 5.5 or less, or more preferably 5 or less. Providing the electrolytic solution with the pH stability can suppress the corrosion of any one of the various members of an electrochemical device. It should be noted that a method of measuring the pH variation will be described later.

As described above, the electrolytic solution of the present invention can achieve an excellent ionic conductivity and excellent pH stability simultaneously. The electrolytic solution of the present invention can be a material which: sufficiently suppresses liquid leakage; has sufficiently suppressed corrosivity against, for example, an electrode; and is stable over time. In addition, the ionic compound described in each of the above sections A-1 to A-3 has a hydrogen atom as a cation, so the ionic compound does not become a strong alkali even in, for example, an environment where a hydroxide ion concentration becomes high. Accordingly, the ionic compound can be sufficiently excellent in performance, durability, and quality, and hence can suitably find use in a variety of applications including materials for electrochemical devices.

<<D. Electrochemical Device>>

Each of the ionic compound of the present invention, the electrolyte material of the present invention, and the electrolytic solution of the present invention can be used as a component of an electrochemical device. The electrochemical device preferably has an ionic conductor, a negative electrode, a positive electrode, a collector, a separator, and a container as basic components.

A mixture of an electrolyte with an organic solvent or a polymer is preferably used as the above-mentioned ionic conductor. The ionic conductor is generally called an "electrolytic solution" when an organic solvent is used, and called "polymer solid electrolyte" when a polymer is used. Polymer solid electrolytes include ones containing an organic solvent as a plasticizer. The above electrolyte can be preferably used as a substitute for the electrolyte or the organic solvent in the electrolytic solution, or as a polymer solid electrolyte in the an ionic conductor. In an electrochemical device prepared using the electrolyte as a material for the ionic conductor, at least one of the materials for the ionic conductor is constituted of the above-mentioned electrolyte. Of those, it is preferred that the electrolyte be used as the substitute for the organic solvent or as the polymer solid electrolyte in the electrolytic solution.

The above-mentioned organic solvent may be an aprotic solvent capable of dissolving the above-mentioned electrolyte, and the above-mentioned organic solvents are preferred as the an organic solvent. However, when two or more solvents are used as a mixed solvent and the electrolyte includes lithium ion, the electrolytic solution is preferably prepared by dissolving the electrolyte in a mixed solvent formed of an aprotic solvent having a permittivity of 20 or more and an aprotic solvent having a permittivity of 10 or less among the organic solvents. Particularly when a lithium salt is used as the electrolyte, the solution has a low solubility in an aprotic solvent having a permittivity of 10 or less, such as diethyl ether or dimethyl carbonate, and therefore a sufficient ionic conductivity cannot be obtained by the solution alone. Conversely, the solution has a high solubility in an aprotic solvent having a permittivity of 20 or more and also has a high viscosity. Therefore, the ions are difficult to migrate and also in this case, a sufficient ionic conductivity cannot be obtained. When those solvents are mixed together, appropriate solubility and migration degree can be secured and sufficient ionic conductivity can be obtained.

As the polymer dissolving the above-mentioned electrolyte, one or more kinds of the above-mentioned polymers can be preferably used. Of those, preferred are polymers or copolymers having polyethlene oxide as a main chain or a side chain, homopolymers or copolymers of polyvinylidene fluoride, methacrylate polymer, and polyacrylonitrile. When a plasticizer is added to those polymers, the above-mentioned aprotic organic solvent may be used.

The electrolyte concentration in the above-mentioned ionic conductor is preferably 0.01 mol/dm$^3$ or more, and equal to a saturation concentration or less. The concentration of less than 0.01 mol/dm$^3$ is undesirable because the ionic conductivity is low. The concentration is more preferably 0.1 mol/dm$^3$ or more and 1.5 mol/dm$^3$ or less.

In lithium batteries, a lithium metal or an alloy of lithium and other metals is preferably used as the material for the above-mentioned negative electrode. For lithium ion batteries, preferred are polymers, organic materials, carbon obtained by baking pitch or the like, natural graphite, and materials prepared by phenomenon called intercalation of metal-oxide or the like. For electric double layer capacitors, preferred are active carbons, porous metal oxides, porous metals, and conductive polymers.

In lithium batteries and lithium ion batteries, preferred materials for the above-mentioned positive electrode are lithium-containing oxides such as $LiCoO_2$, $LiNiO_2$, $LiMnO_2$, and $LiMn_2O_4$; oxides such as $TiO_2$, $V_2O_5$, and $MoO_3$; sulfides such as $TiS_2$ and FeS; and conductive polymers such as polyacetylene, polyparaphenylene, polyaniline, and polypyrrole. For electric double layer capacitors, activate carbons, porous metal oxides, porous metals, and conductive polymers are preferred.

Details about (1) a lithium secondary battery, (2) an electrolytic capacitor, and (3) an electric double layer capacitor, as electrochemical devices, will be described below.

(1) Lithium Secondary Battery

A lithium secondary battery is constituted of, as basic constituent elements, a positive electrode, a negative electrode, separators placed between the positive and negative electrodes, and an ionic conductor containing an electrolyte of the present invention. In this case, the above electrolyte contains a lithium salt as a substance showing ionic conductivity. The a lithium secondary battery is preferably a non-aqueous electrolyte lithium secondary battery other than an aqueous electrolyte lithium secondary battery. FIG. 1 shows a schematic cross-sectional view of an embodiment of the lithium secondary battery. This lithium secondary battery uses coke as a negative electrode active substance mentioned below and a Co-containing compound as a positive electrode active substance. In the a lithium secondary battery, during charging, the reaction of $C_6Li \rightarrow 6C + Li^+ + e^-$ occurs on the negative electrode, the electron (e−) generated on the negative electrode surface migrates through the electrolytic solution to the positive electrode surface in the manner of ionic conduction. On the positive electrode surface, the reaction of $CoO_2 + Li^+ + e^- \rightarrow LiCoO_2$ occurs and an electric current flows from the negative electrode to the positive electrode. During discharging, reverse reactions of those during charging occur, and an electric current flows from the positive electrode to the negative electrode. In this manner, electricity can be stored or supplied by the ion-involving chemical reactions.

The above-mentioned negative electrode is preferably produced by applying a negative electrode mixture containing a negative electrode active substance, a conductive agent for negative electrodes, a binder for negative electrodes, and the like to the surface of a current collector for negative electors. The negative electrode mixture may contain various additives in addition to the conductive agent and the binder.

Metallic lithium and materials capable of occluding and releasing lithium ions are preferred as the above-mentioned negative electrode active substance. Preferred examples of the above-mentioned materials capable of occluding and releasing lithium ions include: metallic lithium; pyrolytic carbons; cokes such as pitch coke, needle coke, and petroleum coke; graphite; glassy carbons; organic polymer-derived baking products produced by baking phenolic resins, furan resins, and the like at an appropriate temperature to convert them into carbon; carbon fibers; carbon materials such as active carbon; polymers such as polyacetylene, polypyrrole, and polyacene; lithium-containing transition metal oxides or transition metal sulfides such as $Li_{4/3}Ti_{5/3}O_4$ and TiS$_2$; metals capable of alloying with alkali metals, such as Al, Pb, Sn, Bi, and Si; cubic intermetallic compounds capable of intercalating alkali metals, such as AlSb, Mg$_2$Si, and NiSi$_2$, and lithium nitrogen compounds such as Li$_{3-x}$G$_x$N (G: transition metal). One or more kinds of them may be used. Of those, metallic lithium and carbonaceous materials capable of occluding and releasing alkali metal ions are more preferred.

The above-mentioned conductive agent for negative electrodes is an electron conductive material. Preferred examples thereof include graphites, for example, natural graphites such as scaly graphite and artificial graphites; carbon blacks such as acetylene black, Ketjen black, channel black, furnace black, lamp black, and thermal black; conductive fibers such as carbon fibers and metal fibers; powder metals such as fluoride carbon, copper, and nickel; and organic conductive materials such as polyphenylene derivatives. One or more kinds of them may be used. Of those, artificial graphites, acetylene black, and carbon fibers are more preferred. The use amount of the conductive agent for negative electrodes is preferably 1 to 50 parts by weight, and more preferably 1 to 30 parts by weight with respect to 100 parts by weight of the negative electrode active substance. The negative electrode active substance has electric conductivity, and therefore the a conductive agent for negative electrodes is not necessarily used.

The above-mentioned binder for negative electrodes may be either a thermoplastic resin or a thermosetting resin. Preferred examples of the a binder for negative electrodes include polyethylene, polypropylene, polytetrafluoroethylene, polyvinylidene fluoride, styrene-butadiene rubbers, tetrafluoroethylene-hexafluoropropylene copolymers, tetrafluoroethylene-perfluoroalkyl vinyl ether copolymers, vinylidene fluoride-hexafluoropropylene copolymers, vinylidene fluoride-chlorotrifluoroethylene copolymers, ethylene-tetrafluoroethylene copolymers, polychlorotrifluoroethylene, vinylidene fluoride-pentafluoropropylene copolymers, propylene-tetrafluoroethylene copolymers, ethylene-chlorotrifluoroethylene copolymers, vinylidene fluoride-hexafluoropropylene-tetrafluoroethylene copolymers, vinylidene fluoride-perfluoromethyl vinyl ether-tetrafluoroethylene copolymers, ethylene-acrylic acid copolymers, ethylene-methacrylic acid copolymers, ethylene-methyl acrylate copolymers, ethylene-methyl methacrylate copolymers, polyamides, polyurethanes, polyimides, polyvinylpyrrolidone, and copolymers thereof. One or more kinds of them may be used. Of those, more preferred are styrene-butadiene rubbers, polyvinylidene fluoride, ethylene-acrylic acid copolymers, ethylene-methacrylic acid copolymers, ethylene-methyl acrylate copolymers, ethylene-methyl methacrylate copolymers, polyamides, polyurethanes, polyimides polyvinylpyrrolidone, and copolymers thereof.

The above-mentioned current collector for negative electrodes is an electron conductor causing no chemical change within the battery. Preferred examples thereof include stainless steel, nickel, copper, titanium, carbon, conductive resins, copper, and stainless steel having a surface on which carbon, nickel, titanium, or the like is attached or filmed-coated. Of those, copper and copper-containing alloys are more preferred. One or more kinds of them may be used. The surface of those current collectors for negative electrodes may be oxidized for use. In addition, it is desirable that the surface of the current collector be provided with projections and depressions. The current collector for negative electrodes is preferably in the form of a foil, film, sheet, net, punched body, lath, porous body, foamed body, molded fiber group, or the like. The current collector preferably has a thickness of 1 to 500 µm.

The above-mentioned positive electrode is preferably produced by applying a positive electrode mixture containing a positive electrode active substance, a conductive agent for positive electrodes, a binder for positive electrodes, and the like to the surface of a current collector for positive electrodes. The positive electrode mixture may contain various additives in addition to the conductor and the binder.

Preferred as the above-mentioned positive electrode active substance are metallic Li, Li$_x$CoO$_2$, Li$_x$NiO$_2$, Li$_x$MnO$_2$, Li$_x$Co$_y$Ni$_{1-y}$O$_2$, Li$_x$Co$_y$J$_{1-y}$O$_z$, Li$_x$Ni$_{1-y}$J$_y$O$_z$, Li$_x$Mn$_2$O$_4$, Li$_x$Mn$_{2-y}$J$_y$O$_4$, and lithium-free oxides such as MnO$_2$, V$_g$O$_h$, and Cr$_g$O$_h$ (g and h each being an integer of 1 or more). One or more kinds of them may be used.

The above J represents at least one element selected from the group consisting of Na, Mg, Sc, Y, Mn, Fe, Co, Ni, Cu, Zn, Al, Cr, Pb, Sb, and B. x satisfies 0≦x≦1.2, y satisfies 0≦y≦0.9, and z satisfies 2.0≦z≦2.3. x varies with charge or discharge of the battery. The following compounds may be used as the positive electrode active substance: transition metal chalcogenides; vanadium oxides or niobium oxides which may contain lithium; conjugated polymer-based organic conductive substances; and Chevrel phase compounds. The positive active substance particles preferably have an average particle diameter of 1 to 30 µm.

The conductive agent for positive electrodes is an electron-conductive material causing no chemical change at charge and discharge potentials for the positive electrode active substance to be used. Preferred examples thereof include: the same materials as in the above-mentioned conductive agent for negative electrodes; powder metals such as aluminum and silver; conductive whiskers such as zinc oxide and potassium titanate; and conductive metal oxides such as titanium oxide. One or more kinds of them may be used. Of those, artificial graphite, acetylene black, and powder nickel are more preferred. The use amount of the conductive agent for positive electrodes is preferably 1 to 50 parts by weight, and more preferably 1 to 30 parts by weight with respect to 100 parts by weight of the positive electrode active substance. When carbon black or graphite is used, the use amount is preferably 2 to 15 parts by weight with respect to 100 parts by weight of the positive electrode active substance.

The above-mentioned binder for positive electrodes may be either a thermoplastic resin or a thermosetting resin. Preferred examples thereof include: those mentioned above in the binder for negative electrodes, except for styrene-butadiene rubbers; and tetrafluoroethylene-hexafluoroethylene copolymers. One or more kinds of them may be used. Of those, polyvinylidene fluoride and polytetrafluoroethylene are more preferred.

The above-mentioned current collector for positive electrodes is an electron conductor causing no chemical change at charge and discharge potentials for the positive electrode active substance to be used. Preferred examples thereof include stainless steel, aluminum, titanium, carbon, conductive resins, aluminum, and stainless steel having a surface on which carbon, nickel, and the like is attached or filmed-coated. One or more kinds of them may be used. Of those, aluminum and aluminum-containing alloys are preferred. The surface of those current collectors for positive electrodes may be oxidized for use. In addition, it is preferred that the surface of the current collector be provided with projections and depressions. The current collector for positive electrodes has the same form and thickness as mentioned above in the current collector for negative electrodes.

Each of the above-mentioned separators is preferably made of a microporous insulating thin membrane showing a high ion permeability and a predetermined mechanical strength when an electrolytic solution is used as the ionic conductor. It is also preferred that the separators have a function of closing the pores at temperatures exceeding a certain temperature and thereby increasing the resistance. The following materials are preferably used as a material for the separators in view of organic solvent resistance and hydrophobicity: porous synthetic resin films made of a polyolefin polymer such as polyethylene or polypropylene; woven or nonwoven fabrics made of an organic material such as polypropylene or fluorinated polyolefin; and woven or nonwoven fabrics made of a glass fiber or an inorganic material. The separator preferably has a pore diameter within a range such that it is impermeable to the positive electrode active substance, the negative electrode active substance, the binders, and the conductive agents separated from the electrodes. The separator preferably has a pore diameter of 0.01 to 1 µm. The separator preferably has a thickness of 10 to 300 µm. The void ratio is preferably 30 to 80%.

The separator surface is preferably modified in advance by corona discharge treatment, plasma discharge treatment, or wet treatment using a surfactant so that the hydrophobicity may be reduced. The treatment can improve the wettability of the separator surface and the inside of the pore, which makes it possible to prevent, to the utmost, the internal resistance of the battery from increasing.

In the constitution of the above-mentioned lithium secondary battery, a gel containing an electrolytic solution-carrying polymer material may be contained in the positive electrode mixture or the negative electrode mixture, or a porous separator made of an electrolytic solution-carrying polymer material may be integrated with the positive electrode or the negative electrode. The polymer material is a material capable of holding the electrolytic solution and is preferably a vinylidene fluoride-hexafluoropropylene copolymer.

Examples of the form of the above-mentioned lithium secondary battery include a coin form, button form, sheet form, laminate form, cylindrical form, flat form, rectangular form, and trapezoidal form for use in an electric vehicle.

(2) Electrolytic Capacitor

The electrolytic solution of the present invention is suitably used in an electrolytic capacitor. The embodiment is a preferred embodiment of the present invention.

Figure 2:
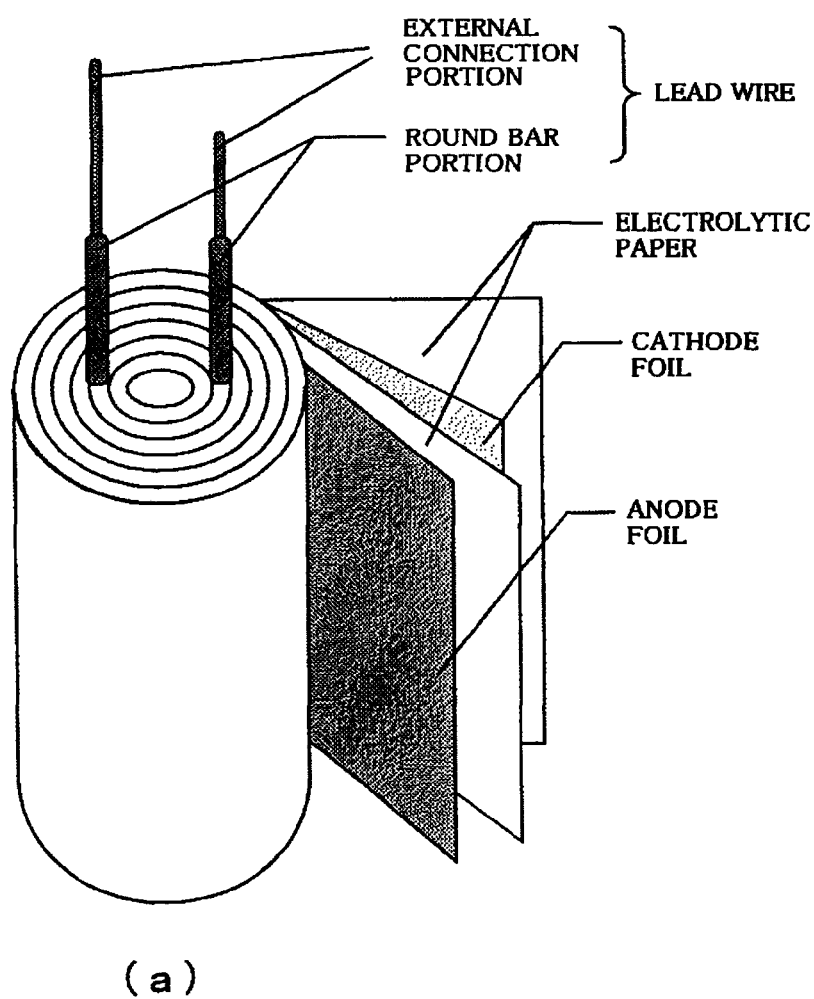
FIG. 2(a) is a perspective view showing one shape of an electrolytic capacitor.
FIG. 2(b) is a schematic sectional view showing one shape of an aluminum electrolytic capacitor.
FIG. 2(c) is a cut front view showing the main portion of the aluminum electrolytic capacitor.
Figure 2:
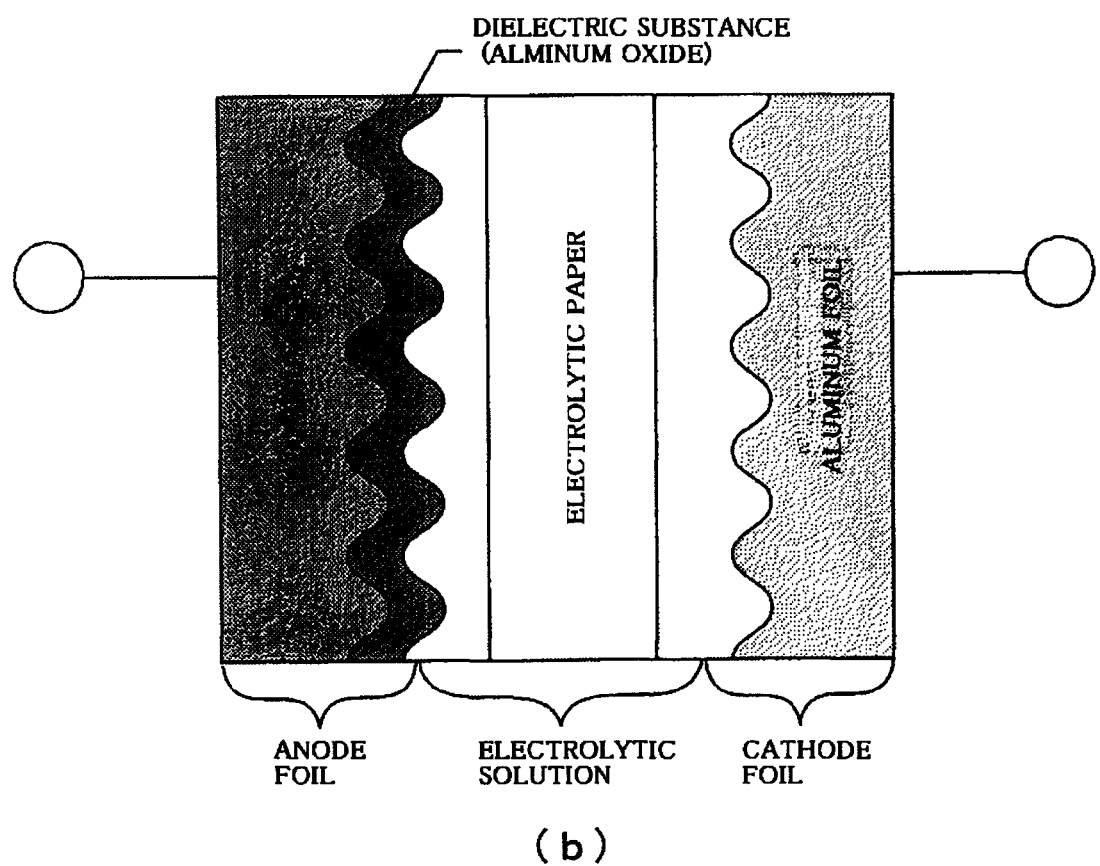
Figure 2:
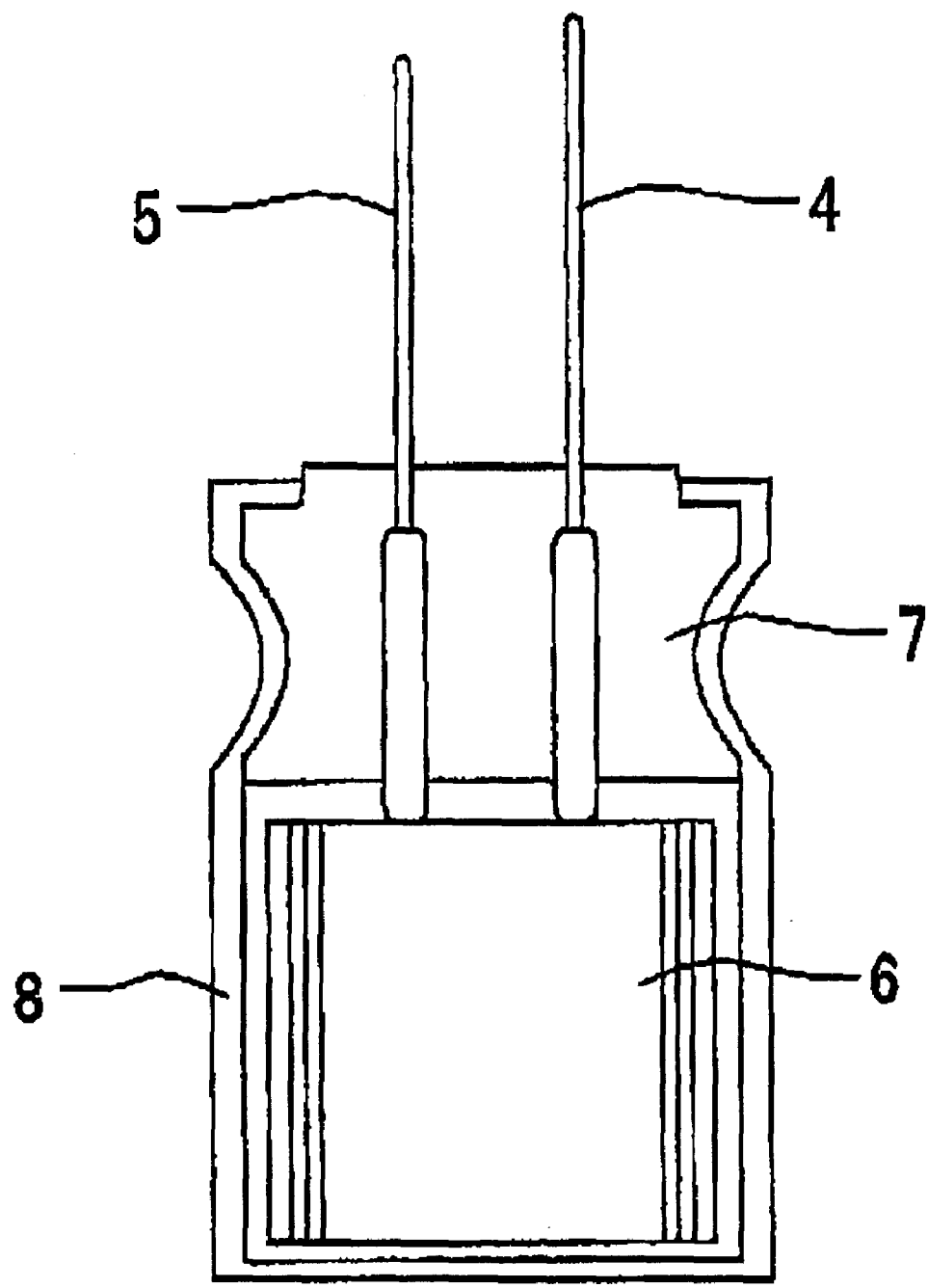

An electrolytic capacitor is constituted of the following basic constituent elements: a capacitor element including an anode foil, a cathode foil, an electrolytic paper sheet sandwiched between the anode foil and cathode foil and serving as a separator, and lead wires; an ionic conductor containing the electrolyte; an exterior case of a cylinder shape with a bottom; and a sealing body for sealing the exterior case. FIG. 2(a) is a perspective view showing an embodiment of the a capacitor element. The electrolytic capacitor of the present invention can be obtained by: impregnating a capacitor element with an electrolytic solution containing the above-mentioned electrolyte material, which serves as an ionic conductor; accommodating the capacitor element in the exterior case of a cylinder shape with a bottom; attaching the sealing body to an opening part of the exterior case; and subjecting an end part of the exterior case to drawing process, thereby sealing the exterior case. Preferred examples of the an electrolytic capacitor include an aluminum electrolytic capacitor, a tantalate electrolytic capacitor, and a niobium electrolytic capacitor. FIG. 2(b) is across-sectional view schematically showing an embodiment of the an aluminum electrolytic capacitor. A preferred form of the an aluminum electrolytic capacitor is a thin oxide (aluminum oxide) film which serves as a dielectric formed by electrolytic anodic oxidation, on the aluminum foil surface roughened finely by providing with projections and depressions by electrolytic etching or deposition.

In addition, FIG. 2(c) shows the cut surface of the main portion of the aluminum electrolytic capacitor. The structure shown in FIG. 2(c) is as described below. An element 6 is formed by winding an anode foil 1 and a cathode foil 2 each subjected to a surface roughening treatment and an oxide film forming treatment through a separator 3. After having been impregnated with an electrolytic solution for driving (hereinafter referred to as "electrolytic solution"), the element is stored in a closed-end cylindrical exterior case 8. An anode extraction lead 4 and a cathode extraction lead 5 are each inserted into and extracted from a through-hole formed in an elastic sealing body 7, and the opening portion of the exterior case is mounted, and hermetically sealed by drawing, with the elastic sealing body 7.

Figure 3:
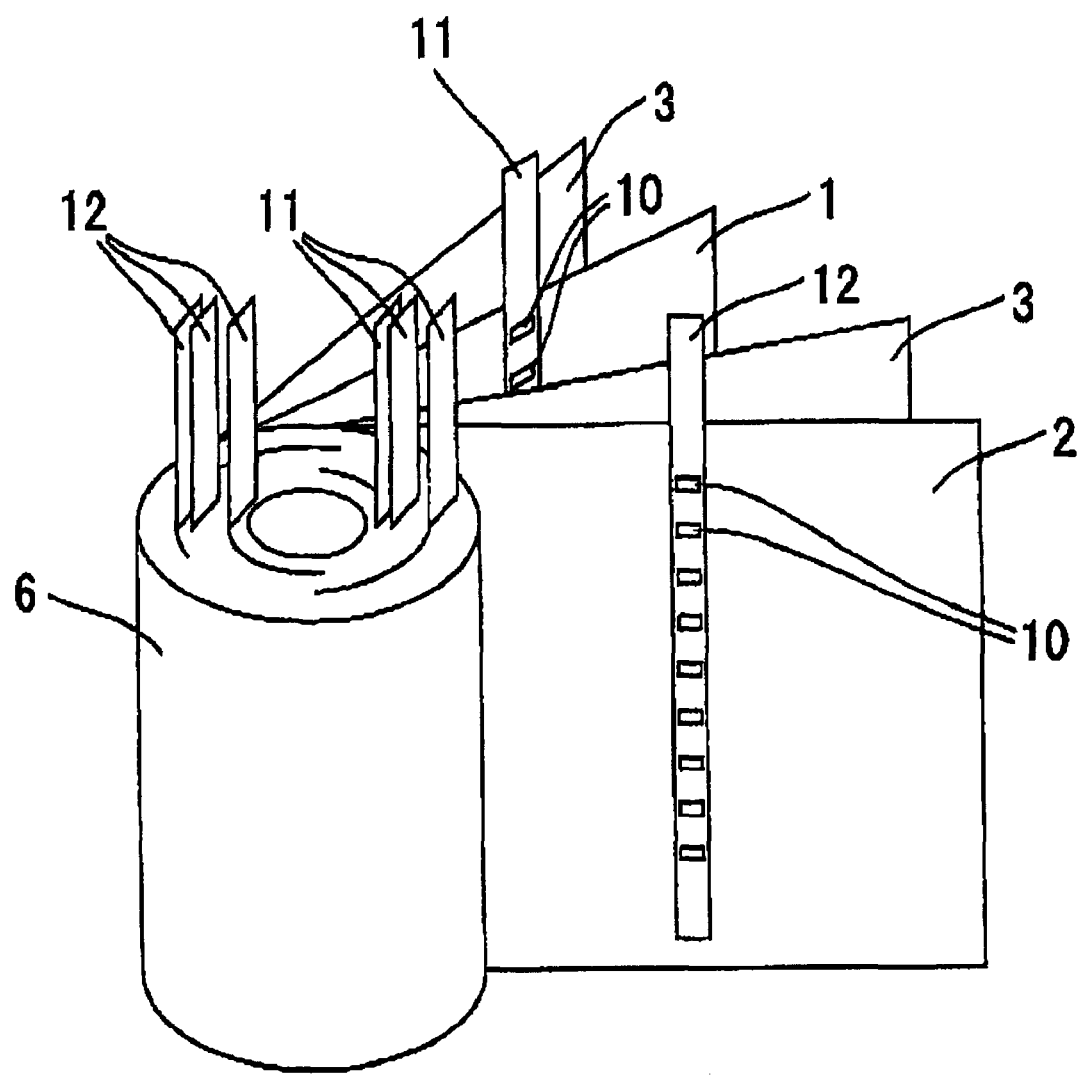
FIG. 3 is an exploded perspective view of an aluminum electrolytic element with another shape.
Figure 4:
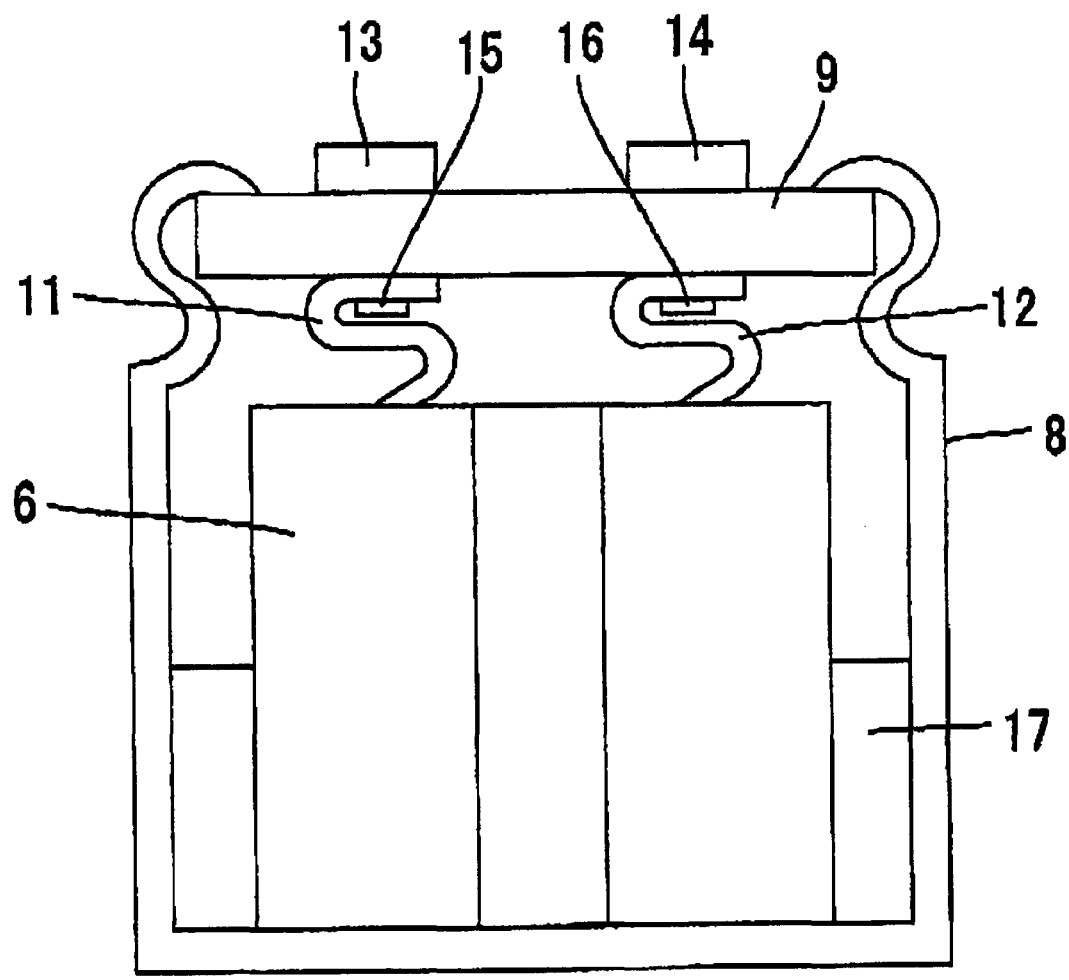
FIG. 4 is a cut front view showing the main portion of the aluminum electrolytic capacitor with the other shape.

An aluminum electrolytic capacitor is generally formed of the structure as shown in each of FIGS. 3 and 4. The element 6 is formed by winding the anode foil 1 and the cathode foil 2 each subjected to an etching treatment and an oxide film forming treatment through the separator 3. After having been impregnated with an electrolytic solution, the element is stored in the closed-end cylindrical exterior case 8. The opening portion of the exterior case 8 is mounted, and hermetically sealed by drawing, with a sealing body 9. The exterior case 8 may have a device fixing agent 17 for fixing the element 6. An anode terminal 13 and a cathode terminal 14 are constituted on the outer end face of the sealing body 9, and the lower end portions of those terminals 13 and 14 serving as an anode internal terminal 15 and a cathode internal terminal 16 are electrically connected with an anode tab terminal 11 and a cathode tab terminal 12 extracted from the element 6. Here, a terminal subjected to a chemical conversion treatment is used as the anode tab terminal 11, but a terminal not subjected to any chemical conversion treatment is used as the cathode tab terminal 12. An aluminum foil not subjected to any surface processing is used in each of the tab terminals 11 and 12.

Figure 5:
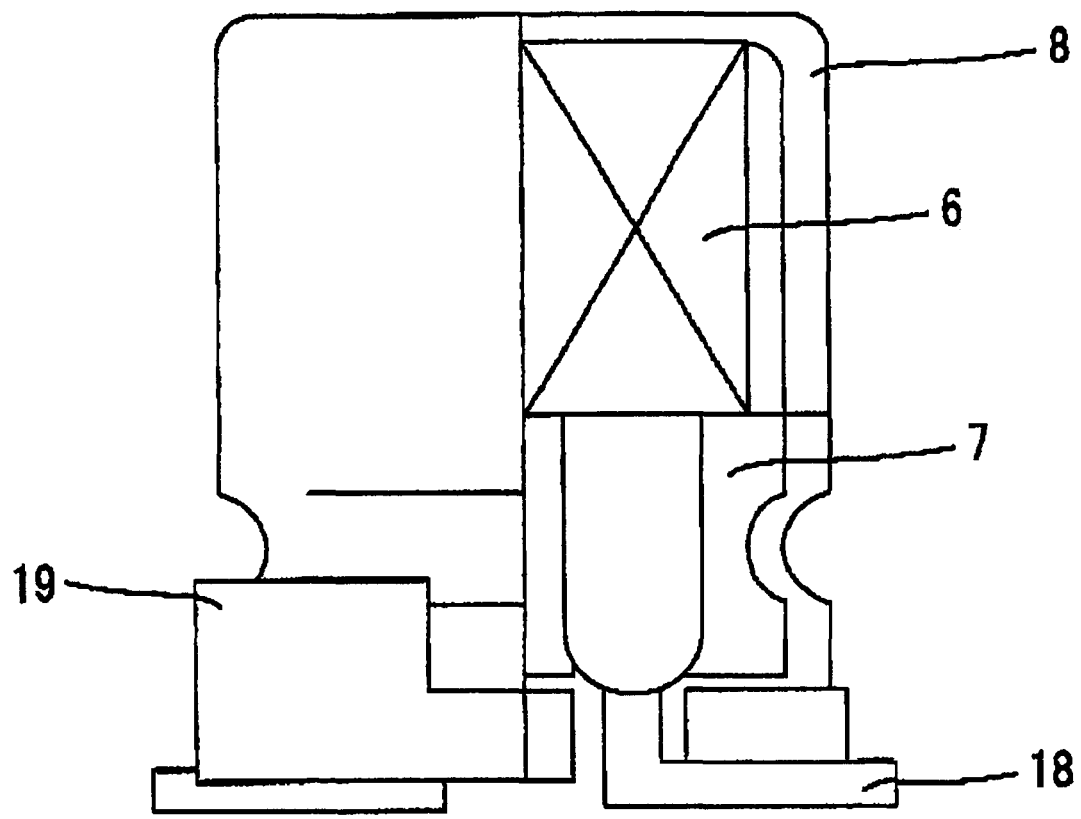
FIG. 5 is a cut front view showing the main portion of a chip-shaped aluminum electrolytic capacitor.

In association with reductions in size and thickness of an electronic part, and the advance of a high-density surface implementation technique, even an aluminum electrolytic capacitor is requested to be of a chip shape. A chip-shaped aluminum electrolytic capacitor is formed of the structure as shown in FIG. 5. The element 6 is formed by winding an anode foil and a cathode foil each subjected to a surface roughening treatment and an oxide film forming treatment through a separator. After having been impregnated with an electrolytic solution, the element is stored in the closed-end cylindrical exterior case 8, and the opening portion of the exterior case 8 is sealed with the elastic sealing body 7, whereby the aluminum electrolytic capacitor is constituted. An insulating plate 19 which: is placed so as to be in contact with an end face from which a lead terminal 18 of the aluminum electrolytic capacitor is extracted; and is provided with a through-hole through which the lead terminal 18 penetrates is mounted to provide the a constitution that the capacitor can be stably mounted on a substrate.

The structure of an aluminum electrolytic capacitor using an electrolytic solution containing the ionic compound described in the above section A-1, the above section A-2, or the above section A-3 may be used as the structure of a newly proposed aluminum electrolytic capacitor, and an example of the capacitor is an aluminum electrolytic capacitor having a structure formed by laminating an anode foil and a cathode foil each subjected to an etching treatment and an oxide film forming treatment through a separator.

The above-mentioned anode foil may be obtained by: chemically or electrochemically etching an aluminum foil having a purity of 99% or more in an acidic solution to perform plane extending treatment; performing formation treatment in an aqueous solution of ammonium borate, ammonium phosphate, ammonium adipate, or the like; and forming an anode oxidized film layer on the surface.

The above-mentioned cathode foil may be prepared by forming, on a part or all of a surface of an aluminum foil, a film made of one or more kinds of metal nitride selected from titanium nitride, zirconium nitride, tantalum nitride, and niobium nitride, and/or one or more kinds of metal selected from titanium, zirconium, tantalum, and niobium.

The above-mentioned film can be formed by a deposition method, a plating method, a coating method, or the like. For the part on which the film is formed, the whole surface of the cathode foil may be covered. As necessary, a part of the cathode foil, for example, only one side of the cathode foil may be covered with a metal nitride or a metal.

Each of the above-mentioned lead wires is preferably constituted of: a connecting part brought into contact with the anode foil and the cathode foil; a round bar part; and an external connecting part. The lead wires are each electrically connected to the anode foil and the cathode foil by means of a stitch, ultrasonic welding, or the like at the connecting parts. The connecting part and the round bar part in the lead wire are preferably made of high purity aluminum. The external connecting part is preferably made of a copper-plated iron steel wire with solder plating. On a part or all of the surface of the round bar and the connecting part with the cathode foil, an aluminum oxide layer formed by anode oxidizing treatment with an aqueous solution of ammonium borate, an aqueous solution of ammonium phosphate, or an aqueous solution of ammonium adipate may be formed. An insulating layer such as a ceramic coating layer made of $Al_2O_3$, $SiO_2$, $ZrO_2$, or the like may be also formed on a part or all of the surface of the round bar part and the connecting part with the cathode foil.

The exterior case is preferably made of aluminum or an aluminum alloy.

The sealing body is provided with through holes from which the lead wires lead out, and preferably made of an elastic rubber such as butyl rubber. The butyl rubber is produced by, for example: adding a reinforcing agent (carbon black or the like), a bulking agent (clay, talc, calcium carbonate, or the like), a process assistance (stearic acid, zinc oxide, or the like), a vulcanizing agent or the like to a crude rubber made of an isobutylene-isoprene copolymer; kneading the mixture; and rolling and molding the resulting mixture. Examples of the vulcanizing agent include: alkylphenol formalin resins; peroxides (dicumyl peroxide, 1,1-di-(t-butylperoxy)-3,3,5-trimethylcyclohexane, 2,5-dimethyl-2,5-di-(t-butylperoxy)hexane, or the like); quinoides (p-quinonedioxime, p,p'-dibenzoylquinonedioxime, or the like); and sulfur. It is more preferred that the surface of the sealing body be coated with a resin such as Teflon (registered trademark), or a plate of bakelite or the like be applied thereto, thereby reducing permeability of solvent steam.

As the above-mentioned separator, paper such as manila paper and kraft paper is usually used, and a non-woven fabric of glass fibers, polypropylene, polyethylene, or the like may be used.

The above-mentioned electrolytic capacitor may be of a hermetic sealing structure, or of a structure in which the capacitor is sealed in a resin case (described, for example, in JP 8-148384 A). In the case of an aluminum electrolytic capacitor having a rubber sealing structure, gas is permeated through the rubber to some extent. Therefore, there is a fear that the solvent may be volatilized from the interior of the capacitor into the air under a high temperature environment, or moisture may be mixed into the interior of the capacitor from the air under a high temperature and high humidity environment. Under the severe environments, the capacitor causes unpreferable changes in properties, such as reduction in electrostatic capacity. In contrast, in the capacitor of a hermetic sealing structure or a structure in which the capacitor is sealed into a resin case, a permeation amount of gas is extremely small. Therefore, the a capacitor exhibits stable properties even under the severe environments.

(3) Electric Double Layer Capacitor

Figure 6:
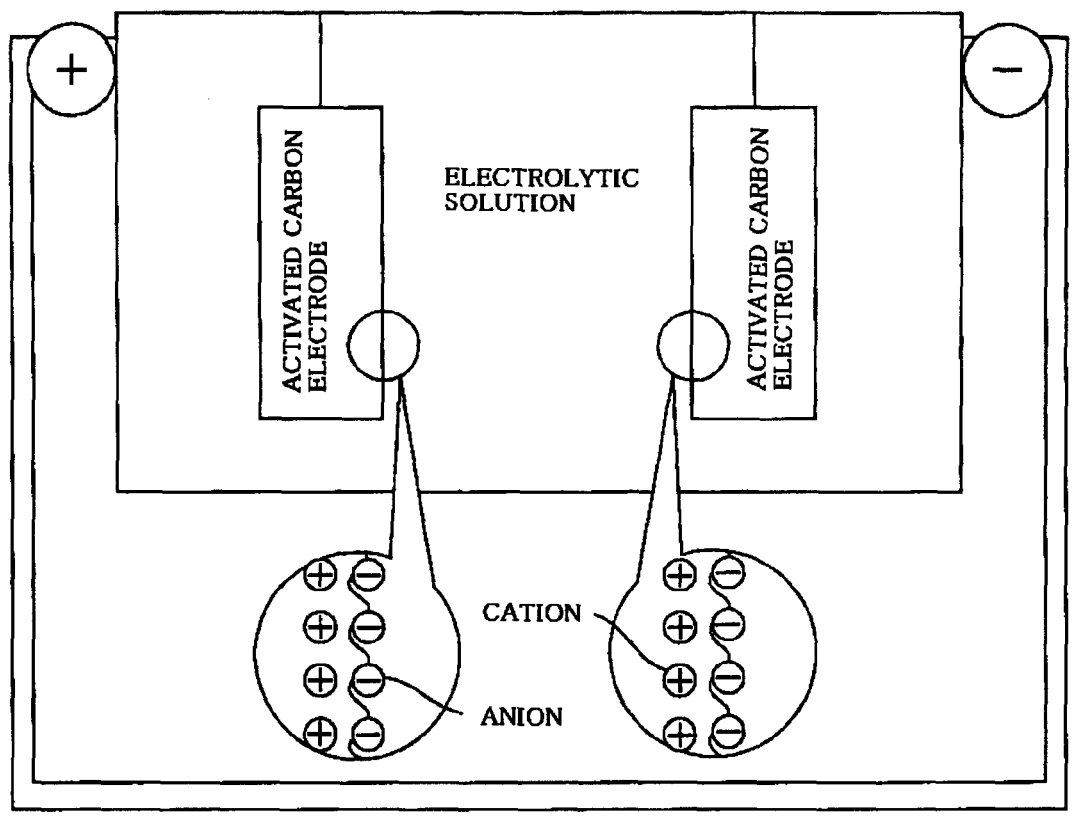
FIG. 6 is a schematic sectional view showing one shape of an electric double layer capacitor and an enlarged schematic view of the surface of an electrode.

An electric double layer capacitor is constituted of the following basic constituent elements: a negative electrode, a positive electrode, and an ionic conductor containing the electrolyte. In a preferred form, an electrolytic solution, as the ionic conductor, is contained in an electrode element formed of the positive electrode and the negative electrode opposed to each other. FIG. 6 shows a schematic sectional view of an embodiment of the an electric double layer capacitor and an enlargement view of the electrode surface.

Each of the above-mentioned positive electrode and negative electrode is a polarizable electrode. Each of the electrodes is constituted of: active carbon serving as an electrode active substance, such as active carbon fibers, a molding of active carbon particles, or active carbon particles; a conductive agent; and a binder substance, and is preferably used in the a molded form as a thin coat film, a sheet, or a plate. In the electric double layer capacitor having the a configuration, an electric charge is stored in the electric double layer formed at the interfaces between the polarizable electrodes and the electrolytic solution as a result of physical adsorption and desorption of ions, as shown in the enlargement view of FIG. 6.

The above-mentioned active carbon preferably has an average pore diameter of 2.5 nm or less. This average pore diameter of the active carbon is preferably measured by the nitrogen adsorption BET method. The specific surface area of the active carbon varies with the electrostatic capacity of the carbonaceous species per unit area ($F/m^2$) or with decrease in bulk density due to increase in specific surface area. The specific surface area determined by the nitrogen adsorption BET method is preferably 500 to 2,500 $m^2/g$, and more preferably 1,000 to 2,000 $m^2/g$.

The above-mentioned active carbon is preferably produced by the following activation method. The activation method includes carbonizing raw materials described below and then activating the carbonated substance. Examples of the raw materials include: plant materials such as wood, sawdust, coconut shells, or pulping waste liquids; fossil fuel materials such as coal, heavy petroleum oils; or pyrolyzates derived therefrom, e.g., coal pitch, petroleum pitch, petroleum coke, carbon aerogel, mesophase carbon, tar pitch fibers; synthetic polymers, phenol resins, furan resins, polyvinyl chloride resins, polyvinylidene chloride resins, polyimide resins, polyamide resins, ion exchange resins, liquid crystal polymers; plastic wastes; and waste tires.

The above-mentioned activation method includes the following methods: (1) gas activation method in which the carbonized raw material is brought into contact with steam, carbon oxide gas, oxygen, or other oxidizing gas and thereby reacted with each other at high temperatures; and (2) chemical activation method in which the carbonized raw material is homogeneously impregnated with zinc chloride, phosphoric acid, sodium phosphate, calcium chloride, potassium sulfide, potassium hydroxide, sodium hydroxide, potassium carbonate, sodium carbonate, sodium sulfate, potassium sulfate, calcium carbonate, boric acid, or nitric acid, and then the mixture is heated in an inert gas atmosphere, to give active carbon as a result of dehydration and oxidation reactions in the presence of a chemical. Either of the methods may be used.

It is preferred that the active carbon obtained by the above-mentioned activation method be thermally treated in an inert gas atmosphere such as nitrogen, argon, helium, or xenon at preferably 500 to 2,500° C. and more preferably 700 to 1,500° C., to thereby eliminate unnecessary surface functional groups or develop the crystallinity of the carbon to increase the electronic conductivity. The active carbon may be in a crushed, granulated, granular, fibrous, felt-like, woven, or sheet form, for instance. When the active carbon is in a granular form, it preferably has an average grain diameter of 30 μm or less from the viewpoint of improvement in the electrode bulk density and reduction in the internal resistance.

Besides the active carbons, carbonaceous materials having the a high specific surface area as mentioned above may be used as the electrode active substance. For example, carbon nanotubes or diamond produced by plasma CVD also may be used.

Preferred examples of the above-mentioned conductive agent include carbon black such as acetylene black or Ketjen black, and metal fibers of natural graphite, thermally expansible graphite, carbon fibers, ruthenium oxide, titanium oxide, aluminum, or nickel. One or more kinds of them may be used. Of those, acetylene black and Ketjen black are more preferred with view to effectively improving the conductivity in small amounts. The mixing amount of the conductive agent varies depending on the bulk density of the active carbon and the like, but is preferably 5 to 50% by weight, and more preferably 10 to 30% by weight, with respect to 100% by weight of the active carbon.

Preferred examples of the above-mentioned binder substance include polytetrafluoroethylene, polyvinylidene fluoride, carboxymethylcellulose, fluoroolefin copolymer crosslinked polymers, polyvinyl alcohol, polyacrylic acid, polyimides, petroleum pitch, coal pitch, and phenol resins. One or more kinds of them may be used. The mixing amount of the binder substance varies depending on the active carbon species and the form thereof, but is preferably 0.5 to 30% by weight, and more preferably 2 to 30% by weight, with respect to 100% by weight of the active carbon.

Each of the above-mentioned positive electrode and negative electrode is preferably molded by the following methods: (1) a method in which polytetrafluoroethylene is added to and mixed with a mixture of the active carbon and acetylene black, and the resulting mixture is molded by pressing; (2) a method in which the active carbon and the binder substance such as pitch, tar, and phenolic resin, and the mixture is molded, and the molding was thermally treated in an inert atmosphere to give a sinter; and (3) a method in which the active carbon and the binder substance are, or only the active carbon is sintered to form an electrode. When an active carbon fiber cloth obtained by activation treatment of a carbon fiber cloth is used, the cloth may be used as it is as an electrode without using any binder substance.

In the above-mentioned electric double layer capacitor, the polarizable electrodes are preferably prevented from contacting or short-circuiting with each other by inserting a separator between the polarizable electrodes or by opposing the polarizable electrodes with a space between them using a holding means, for instance. Suited for use as the separator are porous thin films causing no chemical reactions with the molten salt and the like in the temperature range for use. Suitable separator materials are paper, polypropylene, polyethylene, glass fibers, and the like.

The form of the above-mentioned electric double layer capacitor includes a coin type, wound type, rectangular type, and aluminum laminate type, and any of them may be employed.

The present invention is described in more detail below with reference to Examples, but the present invention is not limited to the following Examples. The term "part" represents "part by weight" and "%" represents "% by weight" unless otherwise specified.

EXAMPLE 1

41.2 g (0.24 mol) of silver nitrate and 250 ml of ion-exchanged water were added to a flask provided with a temperature gauge, a nitrogen gas-introducing pipe, a reflux condenser tube, a stirring device, and a dropping funnel, and the whole was stirred so that silver nitrate would be completely dissolved. Next, a 30% aqueous solution of 26.1 g (0.20 mol) of potassium tricyanomethide (hereinafter referred to as "KTCM") was charged into the dropping funnel, and was dropped to the silver nitrate solution at room temperature over 1 hour. The resultant white solid was separated by filtration and washed with 300 ml of ion-exchanged water. The washing step was repeated 5 times.

Next, 300 ml of ion-exchanged water were added to the white solid, and the whole was placed and stirred in a separable flask to be turned into slurry. A 50% aqueous solution of 27.3 g (0.15 mol) of triethylammonium bromide charged into the dropping funnel was dropped to the slurry at room temperature over 1 hour. After the mixture had been stirred at room temperature for an additional 1 hour, the resultant reaction liquid was filtrated with a membrane filter (hydrophilic type, pore size 0.2 μm). The resultant aqueous solution was concentrated with an evaporator, whereby 27.0 g (0.14 mol) of triethylammonium tricyanomethide (hereinafter referred to as "TEATCM") were obtained in 94% yield.

EXAMPLE 2

A column tube was filled with an ion exchange resin (product name: Amberlite IR120-H (120 ml)) sufficiently washed with ion-exchanged water, and a 0.2 mol/l aqueous solution of 19.3 g (0.15 mol) of KTCM was passed through the tube over 4 hours. The resultant aqueous solution was charged into a beaker, and a 50% solution of 30.2 g (0.30 mol) of triethylamine in methanol was added to the solution at room temperature. After the mixture had been stirred for 30 minutes, the resultant aqueous solution was concentrated with an evaporator, whereby 28.5 g (0.15 mol) of TEATCM were obtained in 99% yield.

EXAMPLE 3

Pyridinium tricyanomethide was obtained in 93% yield in the same manner as in Example 2 except that triethylamine was changed to pyridine.

EXAMPLE 4

1-methylpyrrolidinium tricyanomethide was obtained in 95% yield in the same manner as in Example 2 except that triethylamine was changed to methylpyrrolidine.

EXAMPLE 5

N,N-dimethylhexylammonium tricyanomethide was obtained in 93% yield in the same manner as in Example 2 except that triethylamine was changed to N,N-dimethylhexylamine.

EXAMPLE 6

4-aza-1-azonia-[2,2,2]-bicyclooctane tricyanomethide was obtained in 92% yield in the same manner as in Example 2 except that triethylamine was changed to 4-aza-1-azonia-[2,2,2]-bicyclooctane.

EXAMPLE 7

8-aza-1-azaniabicyclo[5,4,0]unde-7-cene tricyanomethide was obtained in 90% yield in the same manner as in Example 1 except that triethylammonium bromide was changed to 8-aza-1-azaniabicyclo[5,4,0]unde-7-cenebromide.

EXAMPLE 8

5-aza-1-azaniabicyclo[4,3,0]non-5-nene tricyanomethide was obtained in 88% yield in the same manner as in Example 1 except that triethylammonium bromide was changed to 5-aza-1-azaniabicyclo[4,3,0]non-5-nene bromide.

EXAMPLE 9

N,N,N',N'-tetramethylguanidinium tricyanomethide was obtained in 91% yield in the same manner as in Example 2 except that triethylamine was changed to N,N,N',N'-tetramethylguanidine.

EXAMPLE 10

Dimethylphenylammonium tricyanomethide was obtained in 95% yield in the same manner as in Example 2 except that triethylamine was changed to dimethylphenylamine.

EXAMPLE 11

N-methylimidazorium tricyanomethide was obtained in 98% yield in the same manner as in Example 2 except that triethylamine was changed to N-methyl imidazole.

EXAMPLE 12

Trimethylammonium tricyanomethide was obtained in 97% yield in the same manner as in Example 2 except that triethylamine was changed to N-methylamine.

EXAMPLE 13

Dimethylammonium tricyanomethide was obtained in 97% yield in the same manner as in Example 2 except that triethylamine was changed to dimethylethylamine.

EXAMPLE 14

3,5,7-triaza-1-azonia-tricyclo[3,3,1,1]decane tricyanomethide was obtained in 97% yield in the same manner as in Example 2 except that triethylamine was changed to 3,5,7-triaza-1-azonia-tricyclo[3,3,1,1]decane.

EXAMPLE 15

Triethylammonium dicyanomethide was obtained in 88% yield in the same manner as in Example 1 except that potassium tricyanomethide was changed to sodium dicyanoamide.

EXAMPLE 16

1-butylpyrrolidium tricyanomethide was obtained in 90% yield in the same manner as in Example 2 except that triethylamine was changed to 1-buthylpyrrolidine.

EXAMPLE 17

Diethylammonium tricyanomethide was obtained in 90% yield in the same manner as in Example 1 except that triethlammonium bromide was changed to diethylammonium bromide.

EXAMPLE 18

Dibuthylammonium tricyanomethide was obtained in 95% yield in the same manner as in Example 2 except that triethylamine was changed to dibuthylamine.

EXAMPLE 19 n-octylammonium tricyanomethide was obtained in 97% yield in the same manner as in Example 2 except that triethylamine was changed to n-octylamine.

COMPARATIVE EXAMPLE 1

Triethylammonium phthalate was used as it was.

COMPARATIVE EXAMPLE 2

Tetraethylammonium phthalate was used as it was.

COMPARATIVE EXAMPLE 3

Imidazolium tricyanomethide was used as it was.
<Evaluation>
Tables 1 and 2 show the ionic conductivity at 25° C., $^1$H-NMR and $^{13}$C-NMR spectral data, and boiling point (b.p.) of each of the compounds of Examples 2 to 19 and Comparative Examples 1 to 3. It should be noted that the ionic conductivity, $^1$H-NMR, and $^{13}$C-NMR were measured under the following conditions.
(Ionic Conductivity)
Measuring device: impedance analyzer SI1260 (manufactured by Solartron)
Method: SUS electrode, complex impedance method
($^1$H-NMR measurement conditions)
Solvent: DMSO
Temperature: Room temperature
Device: GEMINI-200BB gemini2000
Pulse sequence:
Relaxation delay: 1.254 seconds
Pulse: 45.4 degree pulse
Incorporation time: 2.741 seconds
Spectral range: 3000.3 Hz
Number of times of integration: 16 times
Observation H$^1$, 199.9329029 MHz
Data processing
Number of data points 32768
Measurement time 1 minute
($^{13}$C-NMR measurement conditions)
Solvent: DMSO
Temperature: Room temperature
Device: GEMINI-200BB gemini2000
Pulse sequence:
Relaxation delay: 1.000 second Pulse: 44.6 degree pulse
Incorporation time: 1.498 seconds
Spectral range: 12500.0 Hz
Number of times of integration: 13712 times
Observation $C^{13}$, 50.2732453 MHz
Decouple $H^1$, 199.9339080 MHz
Power 41 dB continuously on
WALTZ-16 modulated
Data processing
Line breadth: 1.0 Hz
Number of data points: 65536
Measurement time: 9.5 hours

TABLE 1

|  | Ionic conductivity (mS/cm) | $^1$H-NMR (δ) | $^{13}$C-NMR (δ) | Boiling point (° C.) |
|---|---|---|---|---|
| Example 2 | 50.7 | 8.7[bs, 1H], 3.08[q, 6H], 1.18[t, 9H] | 121.9, 47.2, 9.9, 5.3 | 89 |
| Example 3 | 45.3 | 8.94[d, 2H], 8.61[dd, 1H], 8.07[dd, 2H] | 145.1, 142.6, 126.6, 120.1, 39.3 | 115 |
| Example 4 | 56.6 | 9.4[bs, 1H], 3.5[bs, 2H], 2.9[bs, 2H], 2.82[s, 3H], 2.0[bs, 2H], 1.8[bs, 2H] | 120.2, 54.7, 54.5, 44.7, 22.6, 22.5, 4.5 | 80 |
| Example 5 | 37.6 | 9.14[bs, 1H], 3.02[q, 2H], 2.76[s, 6H], 1.59[dd, 2H], 1.3[m, 6H], 0.88[t, 3H] | 120.6, 56.7, 42.19, 40.6, 25.4, 23.6, 21.8, 13.8, 4.8 | 150 |
| Example 6 | 34 | 9.42[s, 1H], 3.04[s, 12H] | 120.5, 42.9, 5.1 | — |
| Example 7 | 34.6 | 9.49[s, 1H], 3.56[m, 2H], 3.47[t, 2H], 3.24[m, 2H], 2.64[m, 2H], 1.91[qui, 2H], 1.6[m, 6H] | 166.1, 121.1, 54.1, 48.5, 38.3, 32.4, 28.9, 26.6, 23.9, 19.5, 5.1 | — |
| Example 8 | 41.2 | 9.61[s, 1H], 3.61[t, 2H], 3.38[t, 2H], 3.30[m, 2H], 2.81[t, 2H], 2.04[qui, 2H], 1.92[qui, 2H] | 164.0, 120.5, 53.0, 41.9, 37.5, 29.7, 18.2, 18.1, 5.0 | — |
| Example 9 | 36 | 7.76[s, 2H], 2.89[s, 12H] | 161.1, 120.6, 39.5, 4.9 | — |
| Example 10 | 24.5 | 7.5[bs, 4H], 7.4[bs, 1H], 3.15[s, 6H] | 154.8, 144.2, 129.6, 126.6, 120.2, 118.7, 44.3, 5.1 | 193 |

TABLE 2

|  | Ionic conductivity (mS/cm) | $^1$H-NMR (δ) | $^{13}$C-NMR (δ) | Boiling point (° C.) |
|---|---|---|---|---|
| Example 11 | 49.2 | 14.0[bs, 1H], 9.04[s, 1H], 7.68[d, 2H], 3.87[s, 3H] | 135.8, 123.1, 120.5, 119.8, 35.4, 4.8 | 198 |
| Example 12 | 64.3 | 9.92[bs, 1H], 2.77[s, 9H] | 120.5, 44.2, 4.7 | 3 |
| Example 13 | 54.6 | 9.17[bs, 1H], 3.08[q, 6H], 2.75[s, 6H], 1.19[t, 9H], | 120.5, 51.9, 41.6, 9.3, 4.8 | 38 |
| Example 14 | 20.5 | 8.0[bs, 1H], 4.82[s, 12H] | 120.6, 71.2, 4.8 | — |
| Example 15 | 34.6 | 8.9[bs, 1H], 3.09[q, 6H], 1.18[t, 9H] | 123.5, 47.2, 9.9 | 89 |
| Example 16 | 46.6 | 9.3[bs, 1H], 3.5[m, 2H], 3.1[m, 2H], 3.0[m, 2H], 2.0[m, 2H], 1.9[m, 2H], 1.6[m, 2H], 1.3[m, 2H], 0.9[t, 3H] | 120.4, 53.6, 27.2, 22.5, 19.2, 13.3, 4.7 | 160 |
| Example 17 | 56.4 | 8.18[m, 2H], 2.9[q, 4H], 1.16[t, 6H] | 119.9, 40.7, 10.3, 4.1 | 55 |
| Example 18 | 29.6 | 8.1[bs, 2H], 2.88[t, 4H], 1.5[m, 4H], 1.4[m, 4H], 0.92[t, 6H] | 120.5, 46.5, 27.5, 19.2, 13.4, 4.8 | 159 |
| Example 19 | 24.5 | 7.6[bs, 3H], 2.75[t, 2H], 1.5[m, 2H], 1.3[m, 10H], 0.86[t, 3H] | 120.5, 44.0, 31.1, 28.4, 27.0, 25.7, 22.0, 13.9, 4.8 | 177 |
| Comparative Example 1 | 4.1 | 8.2[m, 2H], 7.5[m, 2H], 3.10[q, 6H], 1.17[q, 9H] | 167.9, 135.0, 132.4, 130.2, 47.2, 9.9 | 89 |
| Comparative Example 2 | 6.5 | 8.2[m, 2H], 7.5[m, 2H], 3.3[q, 12H], 1.2[t, 8H] | 167.9, 135.0, 132.4, 130.2, 51.4, 7.1 | — |
| Comparative Example 3 | 30 | 9.04[s, 1H], 7.65[m, 2H], | 173.4, 134.5, 120.6, 4.7 | 256 |

EXAMPLES 20 TO 56 AND COMPARATIVE EXAMPLES 4 TO 6

Electrolytic solutions for use in aluminum electrolytic capacitors each containing a substance described in any one of Examples 2, 11, and 12, and Comparative Examples 1 to 3 described above were each prepared according to the formulation shown in any one of Tables 3 to 5, and the specific resistance at 30° C. of each of the solutions was measured. The specific resistance was measured under the following conditions. Tables 3 to 5 show the results.

(Specific Resistance)
Device: HIOKI 3522 LCR HiTESTER
Measuring frequency: 1 kHz
Measuring temperature: 30° C.

TABLE 3

| | Electrolytic solution composition | Weight (%) | Specific resistance (Ω·cm) |
|---|---|---|---|
| Example 20 | γ-butyrolactone<br>Triethylammonium tricyanomethide | 97.0<br>3.0 | 98 |
| Example 21 | γ-butyrolactone<br>Triethylammonium tricyanomethide | 95.0<br>5.0 | 83 |
| Example 22 | γ-butyrolactone<br>Triethylammonium tricyanomethide | 85.0<br>15.0 | 59 |
| Example 23 | γ-butyrolactone<br>Triethylammonium tricyanomethide | 75.0<br>25.0 | 45 |
| Example 24 | γ-butyrolactone<br>Triethylammonium tricyanomethide | 65.0<br>35.0 | 42 |
| Example 25 | γ-butyrolactone<br>Triethylammonium tricyanomethide | 55.0<br>45.0 | 38 |
| Example 26 | γ-butyrolactone<br>Triethylammonium tricyanomethide | 50.0<br>50.0 | 31 |
| Example 27 | γ-butyrolactone<br>Triethylammonium tricyanomethide | 20.0<br>80.0 | 23 |
| Example 28 | γ-butyrolactone<br>Triethylammonium tricyanomethide | 0.0<br>100.0 | 19 |
| Example 29 | γ-butyrolactone<br>Trimethylammonium tricyanomethide | 97.0<br>3.0 | 96 |
| Example 30 | γ-butyrolactone<br>Trimethylammonium tricyanomethide | 95.0<br>5.0 | 79 |
| Example 31 | γ-butyrolactone<br>Trimethylammonium tricyanomethide | 85.0<br>15.0 | 56 |
| Example 32 | γ-butyrolactone<br>Trimethylammonium tricyanomethide | 75.0<br>25.0 | 42 |
| Example 33 | γ-butyrolactone<br>Trimethylammonium tricyanomethide | 65.0<br>35.0 | 38 |

TABLE 4

| | Electrolytic solution composition | Weight (%) | Specific resistance (Ω·cm) |
|---|---|---|---|
| Example 34 | γ-butyrolactone<br>Trimethylammonium tricyanomethide | 55.0<br>45.0 | 30 |
| Example 35 | γ-butyrolactone<br>Trimethylammonium tricyanomethide | 50.0<br>50.0 | 24 |
| Example 36 | γ-butyrolactone<br>Trimethylammonium tricyanomethide | 20.0<br>80.0 | 20 |
| Example 37 | γ-butyrolactone<br>N-methylimidazolium tricyanomethide | 97.0<br>3.0 | 101 |
| Example 38 | γ-butyrolactone<br>N-methylimidazolium tricyanomethide | 95.0<br>5.0 | 86 |
| Example 39 | γ-butyrolactone<br>N-methylimidazolium tricyanomethide | 85.0<br>15.0 | 65 |
| Example 40 | γ-butyrolactone<br>N-methylimidazolium tricyanomethide | 75.0<br>25.0 | 46 |
| Example 41 | γ-butyrolactone<br>N-methylimidazolium tricyanomethide | 65.0<br>35.0 | 44 |
| Example 42 | γ-butyrolactone<br>N-methylimidazolium tricyanomethide | 55.0<br>45.0 | 39 |
| Example 43 | γ-butyrolactone<br>N-methylimidazolium tricyanomethide | 50.0<br>50.0 | 32 |
| Example 44 | γ-butyrolactone<br>N-methylimidazolium tricyanomethide | 20.0<br>80.0 | 25 |
| Example 45 | γ-butyrolactone<br>Sulfolane<br>Triethylammonium tricyanomethide | 0.0<br>65.0<br>35.0 | 95 |
| Example 46 | γ-butyrolactone<br>3-methylsulfolane<br>Triethylammonium tricyanomethide | 0.0<br>65.0<br>35.0 | 97 |
| Example 47 | γ-butyrolactone<br>Sulfolane<br>Triethylammonium tricyanomethide | 20.0<br>45.0<br>35.0 | 63 |
| Example 48 | γ-butyrolactone<br>Ethylene glycol<br>Triethylammonium tricyanomethide | 55.0<br>10.0<br>35.0 | 50 |

TABLE 5

| | Electrolytic solution composition | Weight (%) | Specific resistance (Ω·cm) |
|---|---|---|---|
| Example 49 | γ-butyrolactone<br>p-nitrobenzoic acid<br>Triethylammonium tricyanomethide | 64.0<br>1.0<br>35.0 | 42 |
| Example 50 | γ-butyrolactone<br>p-nitrobenzoic acid<br>Triethylammonium tricyanomethide | 63.0<br>2.0<br>35.0 | 43 |
| Example 51 | γ-butyrolactone<br>p-nitrobenzyl alcohol<br>Triethylammonium tricyanomethide | 64.0<br>1.0<br>35.0 | 42 |
| Example 52 | γ-butyrolactone<br>p-nitrocresol<br>Triethylammonium tricyanomethide | 64.0<br>1.0<br>35.0 | 43 |
| Example 53 | γ-butyrolactone<br>m-nitroacetophenone<br>Triethylammonium tricyanomethide | 64.0<br>1.0<br>35.0 | 42 |
| Example 54 | γ-butyrolactone<br>Orthophosphoric acid<br>Triethylammonium tricyanomethide | 64.0<br>1.0<br>35.0 | 42 |
| Example 55 | γ-butyrolactone<br>Hypophosphoric acid<br>Triethylammonium tricyanomethide | 64.0<br>1.0<br>35.0 | 42 |
| Example 56 | γ-butyrolactone<br>Isopropyl phosphate<br>Triethylammonium tricyanomethide | 64.0<br>1.0<br>35.0 | 43 |
| Comparative Example 4 | γ-butyrolactone<br>Triethylammonium phthalate | 65.0<br>35.0 | 150 |
| Comparative Example 5 | γ-butyrolactone<br>Tetramethylammonium phthalate | 65.0<br>35.0 | 80 |
| Comparative Example 6 | γ-butyrolactone<br>Imidazolium tricyanomethide | 65.0<br>35.0 | 45 |

As is apparent from Tables 3 to 5, an example of an electrolyte using the ionic compound in the present invention has a reduced specific resistance as compared to those of the comparative examples. The specific resistance of an electrolytic solution using the ionic compound in the present invention increases with decreasing solute concentration; even the electrolytic solution of Example 20 having a solute concentration of 3 weight % has a reduced specific resistance as compared to that of Comparative Example 4, and the extent to which the specific resistance of the electrolytic solution of Example 20 reduces is small but satisfactory as compared to the extent to which the specific resistance of the electrolytic solution of Example 24 having the same solute concentration as that of Comparative Example 4 reduces.

Comparison between a quaternary ammonium salt electrolytic solution shown in Comparative Example 5 and each of the electrolytic solutions of Examples 24 and 33 each having the same solute concentration as that of Comparative Example 5 shows that an example of an electrolytic solution using the ionic compound in the present invention realizes a sufficient reduction in specific resistance in spite of the fact that the solute of the electrolytic solution is a tertiary salt.

In Tables 3 to 5, the electrolytic solutions of Examples 45 to 47 using sulfolanes as solvents each have a reduced specific resistance as compared to that of Comparative Example 4.

In Tables 3 to 5, the electrolytic solution of Example 48 using ethylene glycol as solvent which has a reduced specific resistance as compared to that of Comparative Example 4 and 5.

In Tables 3 to 5, each of the electrolytic solutions of Examples 49 to 53 each containing a nitro compound as an additive does not show any abrupt increase in specific resistance, and has a reduced specific resistance as compared to those of Comparative Examples 4 to 6.

In Tables 3 to 5, each of the electrolytic solutions of Examples 54 to 56 each containing a phosphorus compound as an additive does not show any abrupt increase in specific resistance, and has a reduced specific resistance as compared to those of Comparative Examples 4 to 6.

Next, an aluminum electrolytic capacitor was produced in accordance with the following procedure.

An element was formed by winding an anode foil and a cathode foil each subjected to an etching treatment and an oxide film forming treatment through a Manila hemp-based separator. After having been impregnated with the electrolytic solution, the element was stored in a closed-end cylindrical exterior case formed of aluminum. An anode extraction lead and a cathode extraction lead on each of which a chemical conversion coating was formed were each inserted into and extracted from a through-hole formed in an elastic sealing body made of butyl rubber, and the opening portion of the exterior case was mounted, and hermetically sealed by drawing, with the elastic sealing body made of butyl rubber, whereby an aluminum electrolytic capacitor was produced. A representative example of the structure of the produced aluminum electrolytic capacitor is a structure shown in FIG. 2(c).

Combinations each formed of 20 aluminum electrolytic capacitors each having an element specification of 6.3 V-1, 000 μF (Φ10×12.5 mL) were produced by using one of the electrolytic solutions of Tables 3 to 5 (Examples 22 to 26, 31 to 35, and 39 to 43, and Comparative Examples 4 to 6) uniquely for each combination.

An impedance at 20° C. and 100 kHz, and an equivalent series resistance at 20° C. and 100 kHz were measured for each of Examples 22 to 26, 31 to 35, and 39 to 43, and Comparative Examples 4 to 6 with a HEWLETT PACKARD 4284A PRECISION LCR METER (manufactured by Hewlett-Packard Company). Table 6 shows the results.

TABLE 6

|  | Impedance 20° C. 100 kHz (mΩ) | Equivalent series resistance 20° C. 100 kHz (mΩ) |
| --- | --- | --- |
| Example 22 | 46 | 46 |
| Example 23 | 35 | 33 |
| Example 24 | 33 | 31 |
| Example 25 | 29 | 29 |

TABLE 6-continued

|  | Impedance 20° C. 100 kHz (mΩ) | Equivalent series resistance 20° C. 100 kHz (mΩ) |
| --- | --- | --- |
| Example 26 | 22 | 22 |
| Example 31 | 44 | 44 |
| Example 32 | 33 | 32 |
| Example 33 | 31 | 30 |
| Example 34 | 27 | 27 |
| Example 35 | 21 | 20 |
| Example 39 | 46 | 45 |
| Example 40 | 36 | 36 |
| Example 41 | 30 | 29 |
| Example 42 | 24 | 24 |
| Example 43 | 21 | 20 |
| Comparative Example 4 | 139 | 139 |
| Comparative Example 5 | 67 | 64 |
| Comparative Example 6 | 49 | 49 |

As is apparent from Table 6, an aluminum electrolytic capacitor of any one of the examples of the present invention has a reduced impedance and a reduced equivalent series resistance as compared to those of the comparative examples. Therefore, the ionic compound of the present invention can be used in an aluminum electrolytic capacitor for a low impedance.

Next, the initial properties of an electrostatic capacity at 20° C. and 120 Hz, and tan δ were measured for each of Examples 22 to 26 and 31 to 35, and Comparative Examples 4 and 5, and then a high temperature application test (105° C., 1,000 hours, application of DC 6.3 V) was performed. In addition, five aluminum electrolytic capacitors in each of the corresponding combinations after the measurement of the initial properties, and five other aluminum electrolytic capacitors in each of the corresponding combinations after the high temperature application test were disassembled so that an electrolytic solution would be taken out of each of the capacitors. Then, the water content of an electrolytic solution in each product was measured. Table 7 shows the results of the electrostatic capacity, tan δ, and the water content of an electrolytic solution in each product. It should be noted that the electrostatic capacity, tan δ, and the water content were each measured by the following method.

(Electrostatic Capacity, tan δ)

Measuring device: Agilent 4263B LCR METER (manufactured by Agilent Technologies, Inc)

(Method of Measuring Water Content)

A sample is prepared by: mixing 0.25 g of a measurement sample and 0.75 g of dehydrated acetonitrile in a glow box having a dew point of −80° C. or lower; and collecting 0.5 g of the mixed solution with a sufficiently dried TERUMO Syringe (trade name, 2.5 ml) in the glow box. After that, the water content of the sample is measured with a Karl Fischer moisture meter AQ-7 (trade name, manufactured by Hiranuma Sangyo Corporation).

TABLE 7

|  | Initial properties | | | 1,000 hours after the application of DC 6.3 V at 105° C. | | |
| --- | --- | --- | --- | --- | --- | --- |
|  | Electrostatic capacity (μF) | tanδ | Water content of electrolytic solution in product (%) | Electrostatic capacity (μF) | tanδ | Water content of electrolytic solution in product (%) |
| Example 22 | 998 | 0.056 | 0.72 | 978 | 0.063 | 1.01 |
| Example 23 | 993 | 0.049 | 0.85 | 977 | 0.060 | 1.23 |
| Example 24 | 996 | 0.045 | 0.69 | 977 | 0.052 | 1.04 |
| Example 25 | 996 | 0.039 | 0.72 | 980 | 0.046 | 1.09 |
| Example 26 | 994 | 0.022 | 0.84 | 971 | 0.027 | 1.11 |
| Example 31 | 994 | 0.052 | 0.77 | 979 | 0.061 | 1.06 |
| Example 32 | 997 | 0.046 | 0.80 | 980 | 0.054 | 1.03 |
| Example 33 | 998 | 0.044 | 0.76 | 979 | 0.053 | 1.21 |
| Example 34 | 993 | 0.036 | 0.73 | 977 | 0.044 | 1.18 |
| Example 35 | 996 | 0.021 | 0.88 | 966 | 0.025 | 1.24 |
| Comparative Example 4 | 970 | 0.102 | 0.81 | 951 | 0.163 | 1.15 |
| Comparative Example 5 | 977 | 0.062 | 0.83 | 945 | 0.088 | 1.12 |

As is apparent from Table 7, an increase in tan δ in the high temperature application test is suppressed in each of the examples of the present invention as compared to that in any one of the comparative examples, so the electrolytic solutions of the examples of the present invention show excellent properties.

In one embodiment, a water content in an electrolytic solution in an aluminum electrolytic capacitor is preferably 0.05 to 3 weight % in 100 weight % of the electrolytic solution. When the water content is less than 0.05 weight %, it becomes difficult to manage the water content in the electrolytic solution, and the difficulty may lead to an increase in cost. In addition, when the water content exceeds 3 weight %, the electrolytic solution may be unable to exert electrical stability sufficiently. The lower limit for the water content is preferably 0.07 weight %, and the upper limit for the water content is preferably 2.5 weight %. The lower limit is more preferably 0.1 weight %, and the upper limit is more preferably 2.0 weight %.

Subsequently, combinations each formed of 10 aluminum electrolytic capacitors each having an element specification of 6.3 V-1,000 μF (Φ10×12.5 mL) were produced by using one of the electrolytic solutions of Tables 3 to 5 (Examples 22 to 26, 31 to 35, and 39 to 43, and Comparative Examples 5 and 6) uniquely for each combination. DC 6.3 V was applied to each capacitor for 2,000 hours under high-temperature, high-humidity conditions, specifically, at a temperature of 85° C. and a relative humidity of 85%, and the capacitor was examined for whether liquid leakage from a lead hole portion of a sealing portion occurred. Table 8 shows the results.

TABLE 8

| | Observation of liquid leakage Temperature 85° C., Relative humidity 85%, Application of DC 6.3 V | | | |
| --- | --- | --- | --- | --- |
| | 250 hours after | 500 hours after | 1000 hours after | 2000 hours after |
| Example 22 | No abnormality is observed even after the application for 2,000 hours. | | | |
| Example 23 | No abnormality is observed even after the application for 2,000 hours. | | | |
| Example 24 | No abnormality is observed even after the application for 2,000 hours. | | | |
| Example 25 | No abnormality is observed even after the application for 2,000 hours. | | | |
| Example 26 | No abnormality is observed even after the application for 2,000 hours. | | | |
| Example 31 | No abnormality is observed even after the application for 2,000 hours. | | | |
| Example 32 | No abnormality is observed even after the application for 2,000 hours. | | | |
| Example 33 | No abnormality is observed even after the application for 2,000 hours. | | | |
| Example 34 | No abnormality is observed even after the application for 2,000 hours. | | | |
| Example 35 | No abnormality is observed even after the application for 2,000 hours. | | | |
| Example 39 | No abnormality is observed even after the application for 2,000 hours. | | | |
| Example 40 | No abnormality is observed even after the application for 2,000 hours. | | | |
| Example 41 | No abnormality is observed even after the application for 2,000 hours. | | | |
| Example 42 | No abnormality is observed even after the application for 2,000 hours. | | | |
| Example 43 | No abnormality is observed even after the application for 2,000 hours. | | | |
| Comparative Example 5 | No abnormality is observed. | No abnormality is observed. | The number of products each showing liquid leakage is 3. | The number of products each showing liquid leakage is 7. |
| Comparative Example 6 | No abnormality is observed. | No abnormality is observed. | The number of products each showing liquid leakage is 4. | The number of products each showing liquid leakage is 7. |

As is apparent from Table 8, an aluminum electrolytic capacitor of any one of the examples of the present invention does not show liquid leakage even under a high-humidity condition, and has excellent reliability as compared to that of each aluminum electrolytic capacitor of Comparative Example 5 using a quaternary ammonium salt as a solute.

EXAMPLE 57

An electrolytic solution was obtained by mixing 30 parts of N-ethyl-N'-methylimidazolium tricyanomethide (hereinafter referred to as "EMImTCM"), 5 parts of triethylammonium tricyanomethide (hereinafter referred to as "TEATCM"), 65 parts of γ-butyrolactone (hereinafter referred to as "GBL"), and 2 parts of water.

EXAMPLE 58

An electrolytic solution was obtained by mixing 25 parts of EMImTCM, 10 parts of TEATCM, 65 parts of GBL, and 2 parts of water.

EXAMPLE 59

An electrolytic solution was obtained by mixing 20 parts of EMImTCM, 15 parts of TEATCM, 65 parts of GBL, and 2 parts of water.

EXAMPLE 60

An electrolytic solution was obtained by mixing 30 parts of EMImTCM, 5 parts of triethylammoniumphthalate (hereinafter referred to as "TEAPh"), 65 parts of GBL, and 2 parts of water.

EXAMPLE 61

An electrolytic solution was obtained by mixing 30 parts of N-ethyl-N'-methylimidazolium phthalate, 5 parts of TEATCM, 65 parts of GBL, and 2 parts of water.

EXAMPLE 62

An electrolytic solution was obtained by mixing 30 parts of triethylmethylammonium tricyanomethide, 5 parts of TEATCM, 65 parts of GBL, and 2 parts of water.

EXAMPLE 63

An electrolytic solution was obtained by mixing 25 parts of 1,2,3-trimethylimidazolinium phthalate, 10 parts of TEATCM, 65 parts of GBL, and 2 parts of water.

COMPARATIVE EXAMPLE 7

An electrolytic solution was obtained by mixing 35 parts of EMImTCM, 65 parts of GBL, and 2 parts of water.

COMPARATIVE EXAMPLE 8

An electrolytic solution was obtained by mixing 20 parts of TEAph, 65 parts of GBL, and 0.5 parts of water.

The pH and ionic conductivity of each of the resultant electrolytic solutions were measured. Table 9 summarizes the results of the measurement.

<pH Measurement>

30 mL of each of the electrolytic solutions obtained in the foregoing were charged into an H-type cell provided with a glass barrier. A platinum electrode was immersed in the electrolytic solution, and electrolysis was performed at 20 mA for 4 hours with a DC power supply (manufactured by Matsusada Precision Inc., product number: PL-650-0.1). The pH of the electrolytic solution before the electrolysis was measured with a pH meter (manufactured by IQ Scientific Instruments, Inc., product number: IQ150), and the pH of the electrolytic solution after the electrolysis was measured with the pH meter. A pH variation was calculated from the resultant values.

TABLE 9

|  | pH | | | Ionic conductivity (mS/cm) |
| --- | --- | --- | --- | --- |
|  | Initial stage | 4 hours after | pH variation |  |
| Example 57 | 6.0 | 10.7 | 4.7 | 26 |
| Example 58 | 6.0 | 10.1 | 4.1 | 28 |
| Example 59 | 5.7 | 10.0 | 4.3 | 25 |
| Example 60 | 6.2 | 11.2 | 5.0 | 24 |
| Example 61 | 7.0 | 10.3 | 3.3 | 20 |
| Example 62 | 6.0 | 10.5 | 4.5 | 20 |
| Example 63 | 6.0 | 10.5 | 4.5 | 16 |
| Comparative Example 7 | 6.5 | 14.0 | 7.5 | 30 |
| Comparative Example 8 | 5.5 | 9.1 | 3.6 | 2 |

As is apparent from Table 9, an electrolytic solution of any one of the examples of the present invention was excellent in an ionic conductivity and pH stability. On the other hand, the electrolytic solution of Comparative Example 7 was excellent in an ionic conductivity, but was poor in pH stability. In addition, the electrolytic solution of Comparative Example 8 was excellent in pH stability, but was poor in an ionic conductivity. In view of the foregoing, one can reach a conclusion that an electrolytic solution capable of achieving an excellent ionic conductivity and excellent pH stability simultaneously can be obtained by dissolving two kinds of electrolyte salts each having an anion represented by the above general formula (1) in a solvent. In addition, an electrolytic solution capable of achieving an excellent ionic conductivity and excellent pH stability simultaneously can be obtained by dissolving two kinds of electrolyte salts each having cations represented by the above general formulae (7) and (6) in a solvent.

EXAMPLE 64

3.7 g (1.3 mmol) of trifluoromethylsulfoneimide and 15 ml of methanol were added to a flask provided with a stirring device and a dropping funnel, and the whole was stirred at room temperature. A solution of 1.6 g (16 mmol) of triethylamine in 20 ml of methanol was dropped to the mixture at room temperature over 1 hour. After the completion of the dropping, the resultant solution was stirred for an additional 1 hour, and was then concentrated and dried, whereby 4.9 g of a skin-colored solid (triethylammonium (bis(trifluoromethanesulfoneimide)): TEATFSI) were obtained in 98% yield.

Next, 35 parts of TEATFSI were dissolved in 65 parts of γ-butyrolactone. The measured ionic conductivity of the resultant solution was 29.8 mS/cm.

$^1$H-NMR of TEATFSI was as shown below.

$^1$H-NMR (solvent: d6-DMSO): δ8.82 (bs, 1H), δ3.10 (q, ΔJ=5.2 Hz, 6H), δ1.17 (t, ΔJ=5.2 Hz, 9H).

It should be noted that the present invention is not limited to the examples. An electrolytic solution prepared by dissolving one or more kinds of the above-mentioned various compounds is applicable to an electrolytic capacitor formed of any material and any structure. In addition, the use of the electrolytic solution can exert an effect similar to that of any one of the examples in an electrolytic capacitor with any structure.

Each of the ionic compound, electrolyte material, and electrolytic solution of the present invention can be suitably used in a cell having a charging/discharging mechanism such as a primary cell, a secondary cell, or a fuel cell, or in an electrochemical device such as an electrolytic capacitor, an electric double layer capacitor, a solar cell, or an electrochromic display device. Each of the ionic compound, electrolyte material, and electrolytic solution of the present invention can be particularly suitably used in a lithium secondary cell, an electrolytic capacitor, or an electric double layer capacitor out of them.

Many other modifications will be apparent to and be readily practiced by those skilled in the art without departing from the scope and spirit of the invention. It should therefore be understood that the scope of the appended claims is not intended to be limited by the details of the description but should rather be broadly construed.

What is claimed is:

1. An electrolyte material comprising an ionic compound comprising:
   a tricyanomethide anion and a cation ion represented by the general formula (3):

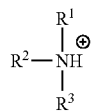

(3)

where $R^1$, $R^2$, and $R^3$ are identical to or different from one another, and each represent a hydrogen element or a hydrocarbon group having 1 to 8 carbon atoms.

2. An electrolyte material comprising an ionic compound comprising:
   an electrolyte salt comprising (i) a tricyanomethide anion and (ii) a tertiary ammonium cation, and
   an electrolyte salt comprising (i) a tricyanomethide anion or a dicarboxylic acid anion and (ii) an onium cation containing nitrogen.

3. An electrolyte material according to claim 1, further comprising an organic solvent.

4. An electrolyte material according to claim 2, further comprising an organic solvent .

5. An electrolyte solution comprising an ionic compound comprising:
   a tricyanomethide anion and a cation ion represented by the general formula (3):

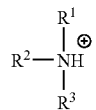

(3)

where $R^1$, $R^2$, and $R^3$ are identical to or different from one another, and each represent a hydrogen element or a hydrocarbon group having 1 to 8 carbon atoms.

6. An electrolyte solution comprising an ionic compound comprising;
   an electrolyte salt comprising (i) a tricyanomethide anion and (ii) a tertiary ammonium cation, and
   an electrolyte salt comprising (i) a tricyanomethide anion or a dicarboxylic acid anion and (ii) an onium cation containing nitrogen.

7. An electrolytic capacitor comprising the electrolytic solution according to claim 5.

8. An electrolytic capacitor comprising the electrolytic solution according to claim 6.

* * * * *